United States Patent [19]
Onishi et al.

[11] Patent Number: 5,814,378
[45] Date of Patent: Sep. 29, 1998

[54] POLYMERIZABLE COMPOUND AND A LIQUID CRYSTAL DISPLAY DEVICE USING THE SAME

[75] Inventors: Noriaki Onishi, Nara; Nobuaki Yamada, Higashiosaka; Kenji Suzuki, Soka; Hoyo Mizobe, Soka; Masahiko Yoshida, Soka, all of Japan

[73] Assignee: Sharp Kabushiki Kaisha, Osaka, Japan

[21] Appl. No.: 678,294

[22] Filed: Jul. 11, 1996

[30] Foreign Application Priority Data

Jul. 11, 1995 [JP] Japan .................................. 7-175264

[51] Int. Cl.⁶ .................................................. G02F 1/1337
[52] U.S. Cl. ................. 428/1; 252/299.01; 252/299.6; 560/221; 560/223; 576/245; 576/246; 349/86; 349/89
[58] Field of Search ................. 252/299.01, 299.6; 428/1; 560/221, 223; 349/86, 89; 526/245, 246

[56] References Cited

U.S. PATENT DOCUMENTS

| | | | |
|---|---|---|---|
| 4,762,912 | 8/1988 | Leslie et al. .......................... 528/503 |
| 5,087,672 | 2/1992 | Babirad et al. ...................... 525/329.5 |
| 5,198,149 | 3/1993 | Reiffenrath et al. ................ 252/299.61 |
| 5,333,074 | 7/1994 | Hikmet . | |
| 5,380,462 | 1/1995 | Kelley et al. ....................... 252/299.63 |
| 5,473,450 | 12/1995 | Yamada . | |
| 5,558,813 | 9/1996 | Akashi et al. ...................... 252/299.01 |
| 5,599,480 | 2/1997 | Tarumi et al. ...................... 252/299.63 |

FOREIGN PATENT DOCUMENTS

| | | |
|---|---|---|
| 58-501631 | 9/1983 | Japan . |
| 61-502128 | 9/1986 | Japan . |
| 1-269 992 A | 10/1989 | Japan . |
| 4-212 928 A | 8/1992 | Japan . |
| 4-338 923 A | 11/1992 | Japan . |
| 5-27 242 A | 2/1993 | Japan . |
| 5-257 135 | 10/1993 | Japan . |
| 6-265 902 A | 9/1994 | Japan . |
| 6-301 015 | 10/1994 | Japan . |
| 6-324 337 | 11/1994 | Japan . |
| WO 83/01016 | 3/1983 | WIPO . |
| WO 85/04262 | 9/1985 | WIPO . |

*Primary Examiner*—Mark Nagumo
*Attorney, Agent, or Firm*—David G. Conlin; Cara Z. Lowen; Dike, Bronstein, Roberts & Cushman, LLP

[57] ABSTRACT

The present invention provides a polymerizable compound represented by Formula (I):

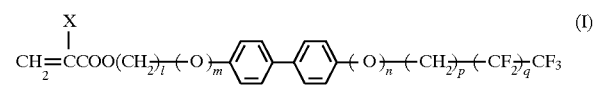

where X represents a hydrogen atom or a methyl group; 1 represents an integer in the range of 0 to 14; m represents 0 or 1; n represents 0 or 1; p represents an integer in the range of 0 to 6; and q represents an integer in the range of 0 to 9, wherein m is 0 under the condition 1=0, and 1 under the condition 1≠0.

9 Claims, 14 Drawing Sheets

Synthesis route 1 where n=1; p=q=0

Synthesis route 2 where n=1;p=0

Synthesis route 3 where n=1; p≠0

Synthesis route 4 where n=0;p=0;q≠0

Synthesis route 5 where n=p=q=0

Synthesis route 6 where n=1;p≠0

Polarizing direction of analyzer

Polarizing direction of polarizer

5,814,378

POLYMERIZABLE COMPOUND AND A LIQUID CRYSTAL DISPLAY DEVICE USING THE SAME

BACKGROUND OF THE INVENTION

1. Field of the Invention

The present invention relates to a polymerizable compound which increases, in a liquid crystal display device including a liquid crystal layer having a polymer region and liquid crystal regions substantially surrounded by the polymer region, the orientation restricting force of liquid crystal molecules at interfaces between the polymer regions and the liquid crystal regions. The present invention also relates to a liquid crystal display device using the polymerizable compound.

2. Description of the Related Art

Liquid crystal display devices using a liquid crystal material and a polymer material:

(I) Japanese National Patent Publication No. 58-501631 discloses a polymer dispersed liquid crystal display device which includes a polymer material and a liquid crystal material encapsulated in the polymer material. This display device displays the scattering state of incident light when no voltage is applied, based on the difference in refractive index between the liquid crystal material and the polymer material. The display device displays a transparent state utilizing the change in the refractive index of the liquid crystal material when a voltage is applied.

Japanese National Laid-open Patent Publication No. 61-502128 discloses a liquid crystal display device including a liquid crystal layer which is formed by irradiating a mixture of a liquid crystal composition (liquid crystal material) and a photocurable resin (polymer material) with UV rays so as to phase-separate the mixture into the liquid crystal material and cured resin in a three-dimensional manner. In principle, these liquid crystal display devices electrically control the scattering (opaque) state and the transmission (transparent) state of light incident to the liquid crystal layer.

(II) Japanese Laid-open Patent Publication No. 1-269922 discloses a technique for forming regions with different characteristics by first radiating UV rays to a liquid crystal layer including a liquid crystal composition (liquid crystal material) and a photocurable resin (polymer material) in a selective manner through a photo-mask, and further irradiating it with UV rays after the photo-mask is removed. The device thus obtained is basically a scattering type device.

Japanese Laid-open Patent Publication No. 5-257135 discloses a device including a liquid crystal layer obtained by: disposing substrates so as to oppose each other with an alignment film having an orientation restricting force being provided on each substrate; injecting a mixture of a liquid crystal material and a photocurable resin in an interspace between the substrates; and irradiating the mixture with UV rays through a photo-mask disposed on either substrate. This device is formed in such a manner that the pattern of the photomask is reflected onto the liquid crystal layer, so as to utilize the different optical characteristics of the liquid crystal regions between the inner portions and outer portions with respect to the photomask when a voltage is applied. This device is a static type liquid crystal device in which the light transmittance of the liquid crystal layer is controlled by applying a voltage between electrodes provided on the substrates, and is to be contrasted to a matrix type liquid crystal display device such as that of the present invention (described later).

The principle of improvement of the viewing angle characteristics of a liquid crystal display device:

In order to improve the viewing angle characteristics of a liquid crystal display device, it is necessary to orient each liquid crystal molecule in three or more different directions within each pixel (liquid crystal region). The principle in the improvement of viewing angle characteristics will be described with reference to FIGS. 13A to 13C and FIGS. 14A to 14C.

FIGS. 13A to 13C are schematic cross-sectional views showing various orientation states of liquid crystal molecules of a liquid crystal display device of a TN mode having no polymer walls. The liquid crystal display device includes opposing substrates 1 and a liquid crystal layer 10 interposed therebetween. Liquid crystal molecules within the liquid crystal layer 10 are aligned along one direction. FIG. 13A shows a state where no voltage is applied to the liquid crystal layer 10; FIG. 13B shows a state where a voltage is applied to the liquid crystal layer 10 so that an intermediate gray scale tone is displayed; and FIG. 13C shows a state where a saturation voltage is applied to the liquid crystal layer 10.

FIGS. 14A to 14C are schematic cross-sectional views showing various orientation states of liquid crystal molecules of a liquid crystal display device including a liquid crystal region surrounded by a polymer wall. The liquid crystal display device includes opposing substrates 1 and a liquid crystal layer 2 interposed therebetween. The liquid crystal layer 2 is composed of a polymer wall 21 and a liquid crystal region 20 surrounded by the polymer wall 21. Liquid crystal molecules within the liquid crystal region 20 are aligned so as to be axially symmetrical with respect to an axis X. FIG. 14A shows a state where no voltage is applied to the liquid crystal layer 2; FIG. 14B shows a state where a voltage is applied to the liquid crystal layer 2 so that an intermediate gray scale tone is displayed; and FIG. 14C shows a state where a saturation voltage is applied to the liquid crystal layer 2.

As seen from FIG. 13B, which shows the TN mode liquid crystal display device having no polymer walls displaying an intermediate gray scale tone, the liquid crystal molecules have different refractive indices when the liquid crystal display device is viewed from direction A and viewed from direction B, thereby leading to varying contrasts depending on the viewing angle. On the other hand, as seen from FIG. 14B, which shows the liquid crystal display device having a liquid crystal region surrounded by a polymer wall displaying an intermediate gray scale tone, the liquid crystal molecules have an axially symmetrical orientation. As a result, the apparent refractive index is averaged or uniform irrespective of whether the display device is viewed from direction A or direction B, thereby leading to substantially the same contrast irrespective of whether the viewing angle is in direction A or direction B.

As seen from above, a liquid crystal display device including liquid crystal molecules having an axially symmetrical orientation (i.e., including liquid crystal regions surrounded by a polymer wall) as shown in FIGS. 14A to 14C has better viewing angle characteristics as compared with the viewing angle characteristics of the TN mode liquid crystal display device shown in FIGS. 13A to 13C.

Specific examples of devices having a wide viewing angle mode:

(1) Japanese Laid-open Patent Publications Nos. 4-338923 and 4-212928 disclose techniques concerning a wide viewing angle mode liquid crystal display device incorporating polarizers along with the above-mentioned polymer dispersed liquid crystal cell, the polarizers being disposed so that the polarization axes of the plates are perpendicular with each other.

(2) As a method for improving the viewing angle characteristics of a non-scattering type liquid crystal display device using a polarizer, Japanese Laid-open Patent Publication No. 5-27242 discloses a method for preparing a composite material of a liquid crystal and a polymer from a mixture of the liquid crystal and a photocurable resin. According to this method, the orientation state of liquid crystal domains become random due to the produced polymer. Therefore, the liquid crystal molecules stand in different directions in each domain when a voltage is applied, so that the apparent refractive indices viewed from different directions become substantially identical. As a result, the viewing angle characteristics when displaying an intermediate gray scale tone are improved.

(3) Japanese Laid-open Patent Publications Nos. 6-265902 and 6-324337 disclose a method for producing a liquid crystal display device with a wide viewing angle mode by performing a concentric or axially symmetrical orientation treatment for each pixel of a substrate of the liquid crystal cell. The essence of these techniques is in the control of liquid crystal molecules of each individual pixel, which requires a complicated process that results in a poor controllability.

(4) In recent years, the present inventors have proposed, in Japanese Laid-open Patent Publication No. 6-301015, a liquid crystal display device having improved viewing angle characteristics. The liquid crystal display device is produced by radiating light on a liquid crystal cell including a liquid crystal composition and a photocurable resin through a photomask. In the resultant liquid crystal display device are formed: liquid crystal regions in which liquid crystal molecules are omnidirectionally (axially symmetrically) oriented in pixels corresponding to light-intercepting portions of the photo-mask; and a polymer wall which consists mainly of the photocurable resin in portions corresponding to the light transmitting portions of the photomask. In this liquid crystal display device, liquid crystal molecules are at an omnidirectional orientation state so that the device operates in accordance with the voltage-respondent behavior illustrated in FIGS. 14A to 14C, thereby achieving remarkably improved viewing angle characteristics.

However, such liquid crystal display devices have a problem in that disclination occurs at interfaces between the polymer wall and the liquid crystal regions due to the reverse tilt of liquid crystal molecules. The disclination, which is displayed as bright lines, degrades the display characteristics in a black state. The disclination lines will now be described with reference to FIG. 15. FIG. 15 is a plan view showing the liquid crystal of FIGS. 14A to 14C in a state where a voltage is applied. The position of the photomask employed during the production of the device is indicated by a broken line 23 in FIG. 15. As seen from FIG. 15, the liquid crystal regions 20 are formed substantially in accordance with the shapes defined by the photomask. With the liquid crystal molecules in the liquid crystal regions 20 being symmetrically oriented with respect to an axis (i.e., axis X in FIG. 14A vertical to the substrate surface), the application of a voltage causes disclination lines 22 to emerge (usually in the periphery or the like of each liquid crystal region 20) due to the reverse tilt of the liquid crystal molecules.

(5) In order to control such disclination occurring with the application of a voltage, the inventors of the present invention have proposed in Japanese Patent Application No. 6-132288 adding a polymerizable compound to a mixture of a liquid crystal composition and a photocurable resin, the polymerizable compound having a molecular structure similar to that of liquid crystal.

However, a liquid crystal display device incorporating such a polymerizable compound is recognized to have the following two problems. Firstly, the brightness of the display device when no voltage is applied decreases due to an increased pretilt of the liquid crystal molecules in liquid crystal regions. Secondly, the response time and the threshold characteristics and steepness of the voltage-transmittance characteristics of the liquid crystal display device become unsatisfactory due to interaction between the liquid crystal molecules and the polymer in polymer-liquid crystal composite regions and at interfaces between the polymer wall and liquid crystal regions, etc.

Furthermore, this type of liquid crystal display device has problems associated with the method for controlling the orientation of the liquid crystal for achieving an omnidirectional orientation within each pixel and the method for preventing the decrease in contrast due to depolarization owing to scattering occurring at interfaces between the liquid crystal and the polymer, which are required for improving the viewing angle characteristics. In theory, the scattering occurring at interfaces between the liquid crystal and the polymer can be reduced by decreasing the area of interfaces between the liquid crystal and the polymer within each pixel. However, in practice, it is very difficult with conventional techniques to control the sizes, positions, and the like of liquid crystal droplets formed in a three-dimensional polymer matrix.

In order to solve the above-mentioned problem, it is necessary to clear the hurdles of orientation control of liquid crystal and restraint of scattering. Accordingly, a liquid crystal display device is desired in which the generation of disclination lines is prevented and which has an excellent response time and voltage-transmittance characteristics and yet is sufficiently bright when no voltage is applied, and a polymerizable compound is desired which makes possible the production of such liquid crystal display devices.

SUMMARY OF THE INVENTION

The present invention provides a polymerizable compound represented by Formula (I):

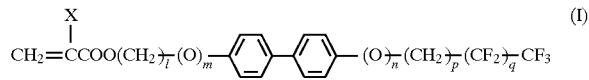

where X represents a hydrogen atom or a methyl group; l represents an integer in the range of 0 to 14; m represents 0 or 1; n represents 0 or 1; p represents an integer in the range of 0 to 6; and q represents an integer in the range of 0 to 9, wherein m is 0 under the condition $l=0$, and 1 under the condition $l\neq 0$.

In one embodiment of the invention, $l\neq 0$ in the above Formula (I).

A liquid crystal display device according to the present invention includes a pair of substrates, at least one of the substrates being transparent, and a liquid crystal layer having a liquid crystal region surrounded by a polymer region, the liquid crystal layer being interposed between the pair of substrates, wherein the polymer region is formed from a monomer at least containing the polymerizable compound represented by Formula (I):

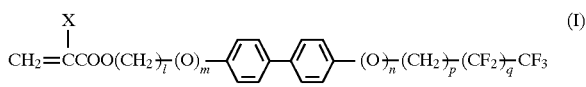

(I)

where X represents a hydrogen atom or a methyl group; 1 represents an integer in the range of 0 to 14; m represents 0 or 1; n represents 0 or 1; p represents an integer in the range of 0 to 6; and q represents an integer in the range of 0 to 9, wherein m is 0 under the condition 1=0, and 1 under the condition 1≠0.

In one embodiment of the invention, 1≠0 in the above Formula (I).

In another embodiment of the invention, liquid crystal molecules in the liquid crystal region have an axially-symmetrical, radial, concentric, random, or spiral orientation.

In still another embodiment of the invention, the polymer region has a function of restricting an orientation state of the liquid crystal molecules on at least one of the pair of substrates.

In still another embodiment of the invention, the liquid crystal display device further includes an insulation film/alignment layer for achieving a uniaxial and uniform orientation state of the liquid crystal molecules corresponding to the liquid crystal region, the insulation film/alignment layer being provided on at least one of the pair of substrates, wherein the orientation state of the liquid crystal region and the entire liquid crystal display device are adapted for a TN, STN, ECB, or an SSFLC mode.

Thus, the present invention makes possible the advantages of: (1) providing a liquid crystal display device in which the generation of disclination lines is prevented and which has an excellent response time and voltage-transmittance characteristics and yet is sufficiently bright when no voltage is applied; and (2) providing a polymerizable compound which makes possible the production of such liquid crystal display devices.

These and other advantages of the present invention will become apparent to those skilled in the art upon reading and understanding the following detailed description with reference to the accompanying figures.

DESCRIPTION OF THE PREFERRED EMBODIMENTS

Figure 1:
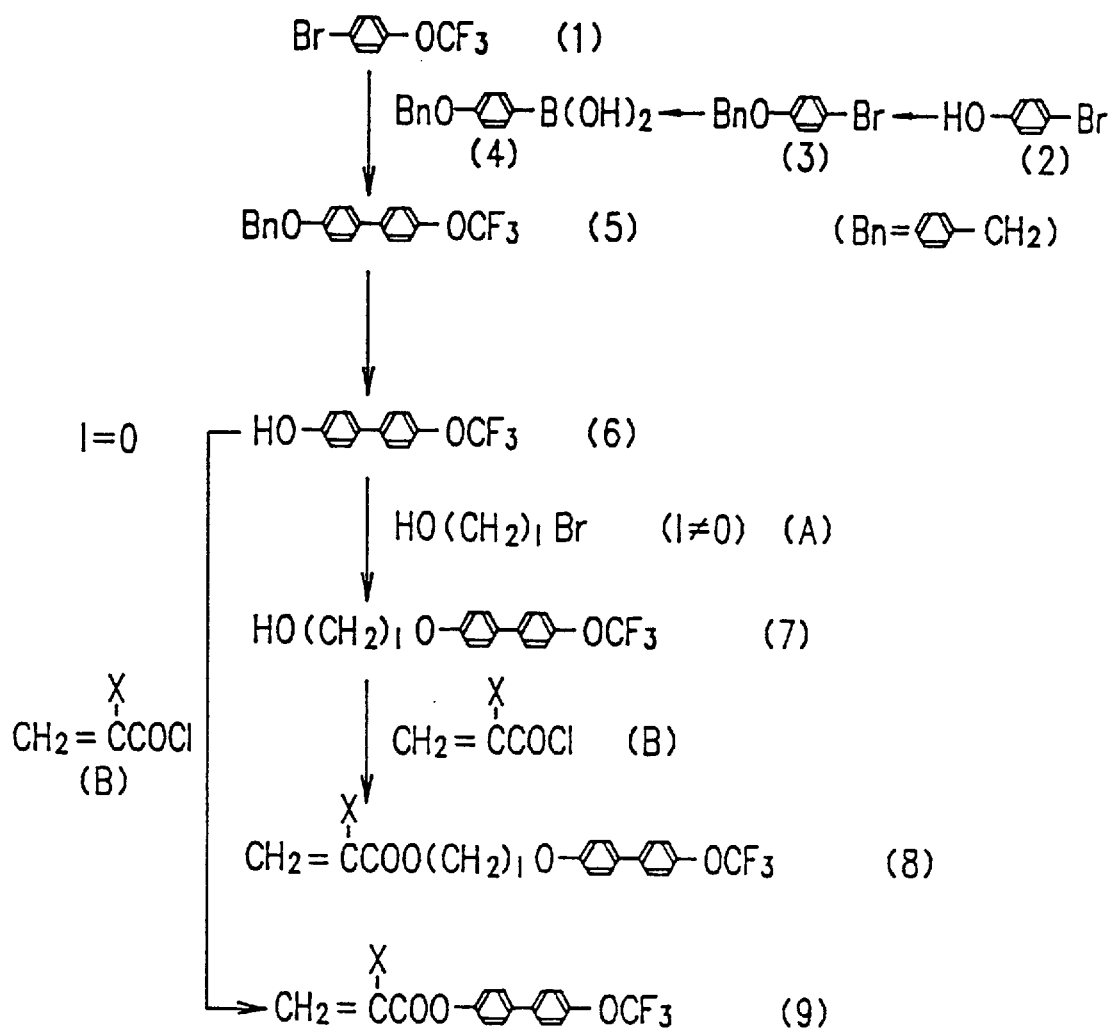
FIG. 1 is a reaction scheme diagram showing an exemplary synthesis route of a polymerizable compound of the present invention.

In the present specification, "a liquid crystal layer including a polymer region and liquid crystal regions surrounded by the polymer region" refers to any liquid crystal layer having a structure in which liquid crystal regions containing liquid crystal molecules are partitioned by polymer where they contact with the polymer. Examples of the above-defined liquid crystal layer include: a liquid crystal layer including liquid crystal regions in which liquid crystal is completely surrounded or enclosed by polymer; a liquid crystal layer including liquid crystal regions partitioned by pillar-like or wall-like polymer structures; and a liquid crystal layer including liquid crystal regions partitioned by a three-dimensional network structure of polymer.

Polymerizable compound

The polymerizable compound of the present invention consists of a number of chemical compounds having within their molecules a structure similar to that of liquid crystal, a polymerizable functional group, and a fluorinated alkyl group.

The polymerizable compound of the present invention (hereinafter referred to as the "present polymerizable compound") preferably has a structure represented by the following Formula (I), although not limited thereto.

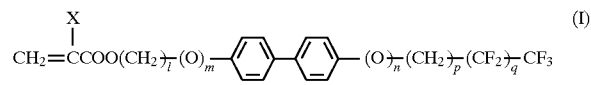

(I)

where X represents a hydrogen atom or a methyl group; 1 represents an integer in the range of 0 to 14; m represents 0 or 1; n represents 0 or 1; p represents an integer in the range of 0 to 6; and q represents an integer in the range of 0 to 9, wherein m is 0 under the condition 1=0, and 1 under the condition 1≠0.

In the above polymerizable compound, an ethylene-type unsaturated group and a fluorinated alkyl group are bonded to a mesogen backbone having liquid crystal properties, with or without a linking group interposed therebetween.

Since the present polymerizable compound includes a mesogen backbone in its molecule, a mesogen backbone is introduced in a polymer formed from a monomer containing the present polymerizable compound. The present polymerizable compound, including a mesogen backbone, provides the following effects:

When a liquid crystal display device of a display mode utilizing orientation restricting force (which is substantially provided by an alignment film formed thereon) of a substrate is produced by using a liquid crystal material and a polymerizable compound, a polymer region formed from the polymerizable compound is formed between the alignment and a liquid crystal region, thereby reducing the orientation restriction force of the alignment film for the liquid crystal molecules. On the other hand, when a mesogen backbone is introduced in the molecule of the polymerizable compound, as in the present polymerizable compound, polymer having a structure similar to that of liquid crystal molecules exists in the polymer region. As a result, the polymer region becomes capable of transmitting the orientation restricting force of the alignment film. Therefore, even if such a polymer region exists between the liquid crystal region and the alignment film, the orientation restricting force of the alignment film is sufficiently transmitted to the liquid crystal molecules within the liquid crystal regions, whereby the orientation state of liquid crystal molecules within the liquid crystal regions is stabilized. Furthermore, the use of the present polymerizable compound causes liquid crystal molecules to have a pretilt, which effectively prevents the generation of disclination lines when a voltage is applied.

The present polymerizable compound includes a fluorinated alkyl group at one end of the molecule. Hereinafter, the effect provided by the fluorinated alkyl group will be described in detail.

In general, a liquid crystal display device produced by utilizing phase separation including a polymerization reaction from a mixture of a liquid crystal and a polymerizable compound is likely to have the problems listed in Table 1.

TABLE 1

| Problems | Estimated Causes |
|---|---|
| Long response time | Dissolution of the resin material, monomers, etc. (i.e., polymerizable compound) in the liquid crystal |
| Hysteresis | Strong anchoring strength of the liquid crystal molecules to the polymer region |
| High driving voltage | Same as above |
| Leakage of light when a saturation voltage is applied | Dissolution of liquid crystal molecules and polymer molecules inside the liquid crystal region, and strong anchoring strength of liquid crystal molecules to the polymer wall. |

The causes of the above-described problems are: the strong anchoring strength of the liquid crystal molecules to the polymer region (i.e., polymer present in the region), as well as the good-compatibility between the polymer (resulting from polymerization of the polymerizable compound) and the liquid crystal material. Both of these problems can be solved by introducing a fluorinated portion in the polymer. Since the fluorinated portion has a different level of surface free energy than that of non-fluorinated portions, the fluorinated portion emerges on the surface of the polymer region. As a result, the surface free energy of the polymer region surface decreases so as to decrease the anchoring strength of liquid crystals, whereby the orientation state of the liquid crystal is stabilized. Moreover, the fluorinated portion has a different level of surface free energy than that of the liquid crystal material, the compatibility between the polymer material and the liquid crystal material decreases. As a result, the response time of the liquid crystal decreases, thereby improving the threshold characteristics of voltage-transmittance characteristics and the steepness of voltage response. Furthermore, since the fluorinated alkyl group is introduced at an end of the molecule of the present polymerizable compound, the anchoring strength and the compatibility between the polymer material and the liquid crystal material further decrease (thereby enabling even faster response and improving the threshold characteristics of voltage-transmittance characteristics and the steepness of voltage response). The reason is that, relative to a fluorinated alkyl group introduced at the central portion of the polymerizable compound or the mesogen backbone, the fluorinated alkyl group introduced at an end of the molecule can more easily move to the surface of the polymer region. Moreover, a larger amount of fluorine can be introduced at an end of the molecule than in the central portion or the mesogen backbone of the molecule.

As the fluorinated portion increases in the polymer molecule, the anchoring strength and the compatibility between the polymer material and the liquid crystal material have a larger decrease. Therefore, in accordance with the present polymerizable compound, q in Formula (I) is preferably an integer in the range of 0 to 9, more preferably in the range of 2 to 8 and most preferably in the range of 3 to 7. If q exceeds 9, the difference in surface free energy between the fluorinated portion polymer and the liquid crystal material becomes too large, possibly resulting in insufficient orientation restriction force of the alignment film to the liquid crystal molecules.

The mesogen backbone of the present polymerizable compound is bonded to an ethylene-type unsaturated group with or without a linking group interposed therebetween. A preferable linking group, if any, is $-(CH_2)_l-(O)_m-$. In the above formula, l is an integer in the range of 0 to 14, and preferably 2 to 12. It is preferable that m is 0 where l is 0. It is preferable that m is 1 where l is not 0. If l exceeds 14, the mesogen portion of the present polymerizable compound projects from the surface of the polymer composing the polymer region surrounding the liquid crystal region to response along with the liquid crystal molecules, for example, thereby increasing the response time. Although the effect of suppressing the generation of disclination lines tends to be more drastic (i.e., effective with only a small amount) as the chain length increases, a longer chain length also increases the pretilt, possibly decreasing the transmittance of the cell.

The mesogen backbone of the present polymerizable compound is bonded to a fluorinated alkyl group with or without a linking group interposed therebetween. A preferable linking group, if any, is $-(O)_n-(CH_2)_p-$. In the above formula, p is an integer in the range of 0 to 6, and preferably 0 to 4. If p exceeds 6, the fluorinated alkyl portion of the present polymerizable compound becomes likely to project from the surface of the polymer composing the polymer region surrounding the liquid crystal region, which in itself makes for the formation of a preferable interface between the polymer region and the liquid crystal region, but the elongated alkyl chain causes the liquid crystal molecules to have a larger pretilt and the heat resistance of the liquid crystal to deteriorate as with changes in the thermal circumstances. Therefore, the value of the length of the alkyl chain p should preferably be in the above-specified range.

When forming a polymer for composing the polymer region surrounding liquid crystal regions by using the present polymerizable compound, the present polymerizable compound can be polymerized alone or copolymerized with another monomer. Examples of "another monomer" to be copolymerized with the present polymerizable compound include bisphenol A dimethacrylate, bisphenol A diacrylate, 1,4-butanediol dimethacrylate, 1,6-hexanediol dimethacrylate, trimethylol propane trimethacrylate, trimethylol propane triacrylate, tetramethylolmethane tetraacrylate, and R-684 (manufactured by Nippon Kayaku Co., Ltd.).

When copolymerized with another monomer, the present polymerizable compound preferably accounts for 3% to 60% by weight, and preferably 3% to 40% by weight, of the overall monomer.

Method of synthesis of the present polymerizable compound

Next, the method for synthesizing the present polymerizable compound will be described. The synthesis routes described below are illustrative examples, and the present invention is not limited thereto.

Synthesis route 1

Synthesis route 1 describes a case where n=1 and p=q=0 in the above general Formula (I), with reference to the reaction scheme shown in FIG. 1.

First, Compound (2) is etherified by a usual method using benzyl bromide:

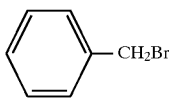

or benzyl chloride:

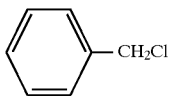

to obtain Compound (3). After allowing B(OCH$_3$)$_3$ to react with a Grignard reagent of Compound (3), Compound (3) is subjected to hydrolysis using dilute sulfuric acid to obtain Compound (4).

Next, Compound (4) and Compound (1) are allowed to have a coupling reaction in the presence of a Pd catalyst to obtain Compound (5). Compound (5) is debenzylated using hydrogen gas to obtain Compound (6). Compound (6) is etherified with Compound (A) to obtain Compound (7). Compound (7) is allowed to react with Compound (B) to obtain Compound (8), which is the target compound.

In the case where no linking group is present between the mesogen group and the ethylene-type unsaturated group (1=0), Compound (B) can be directly allowed to react with Compound (6) to obtain the target Compound (9).

Synthesis route 2

Figure 2:
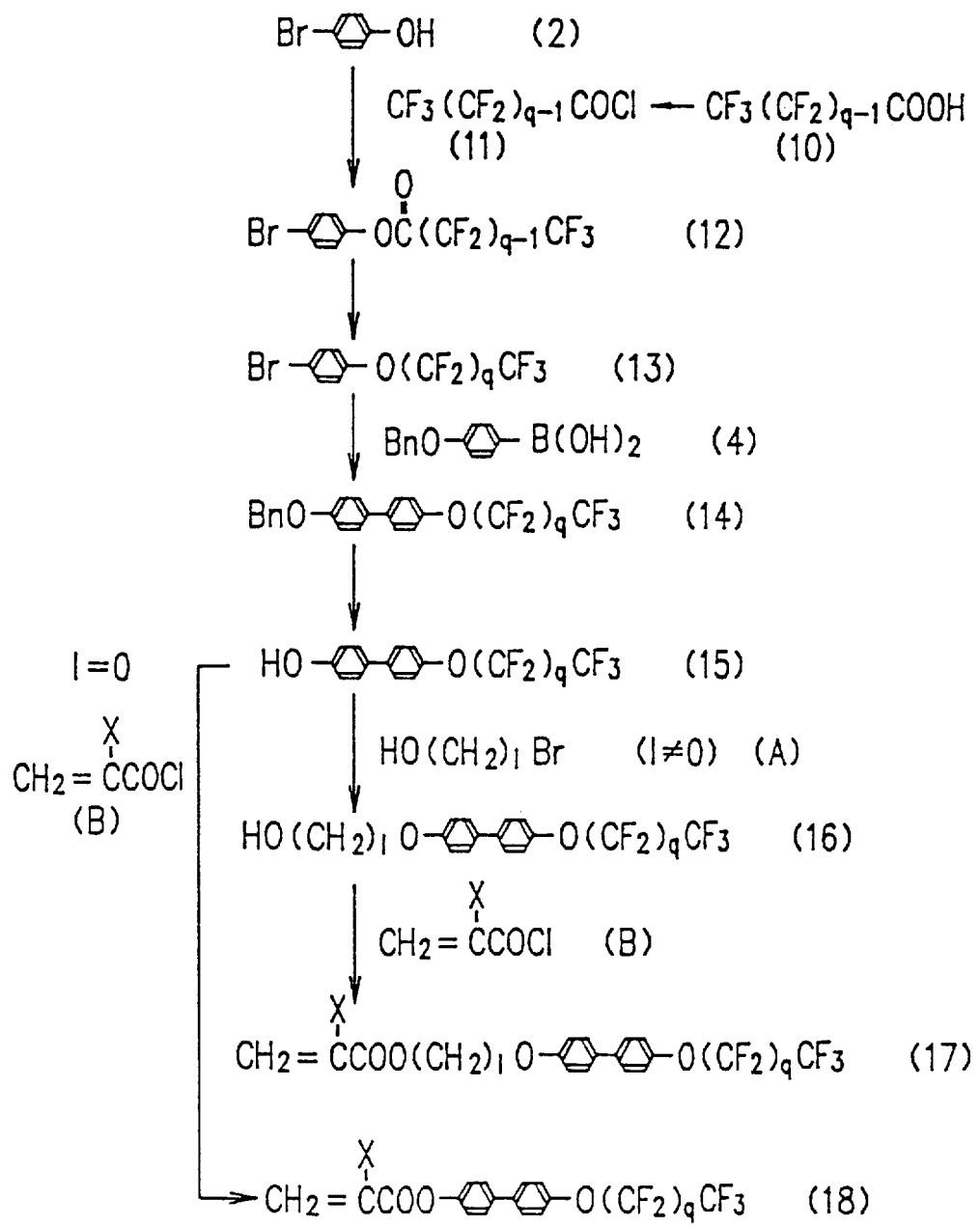
FIG. 2 is a reaction scheme diagram showing another exemplary synthesis route of a polymerizable compound of the present invention.

Synthesis route 2 describes a case where n=1 and p=0 in the above general Formula (I), with reference to the reaction scheme shown in FIG. 2.

First, phosphorus pentachloride is allowed to react with Compound (10) to obtain Compound (11). Compound (11) is esterified with Compound (2) to obtain Compound (12). Compound (12) is fluorinated by a method described in William A. Sheppard et al., J. Org. Chem., 29(1)1(1964) to obtain Compound (13).

Next, Compound (13) and Compound (4) are allowed to have a coupling reaction in the presence of a Pd catalyst to obtain Compound (14). Compound (14) is debenzylated using hydrogen gas in the presence of a Pd catalyst to obtain Compound (15).

Finally, Compound (15) is etherified with Compound (A) to obtain Compound (16). Compound (16) is allowed to react with Compound (B) to obtain Compound (17), which is the target compound.

In the case where no linking group is present between the mesogen group and the ethylene-type unsaturated group (1=0), Compound (B) can be directly allowed to react with Compound (15) to obtain the target Compound (18).

Synthesis route 3

Figure 3:
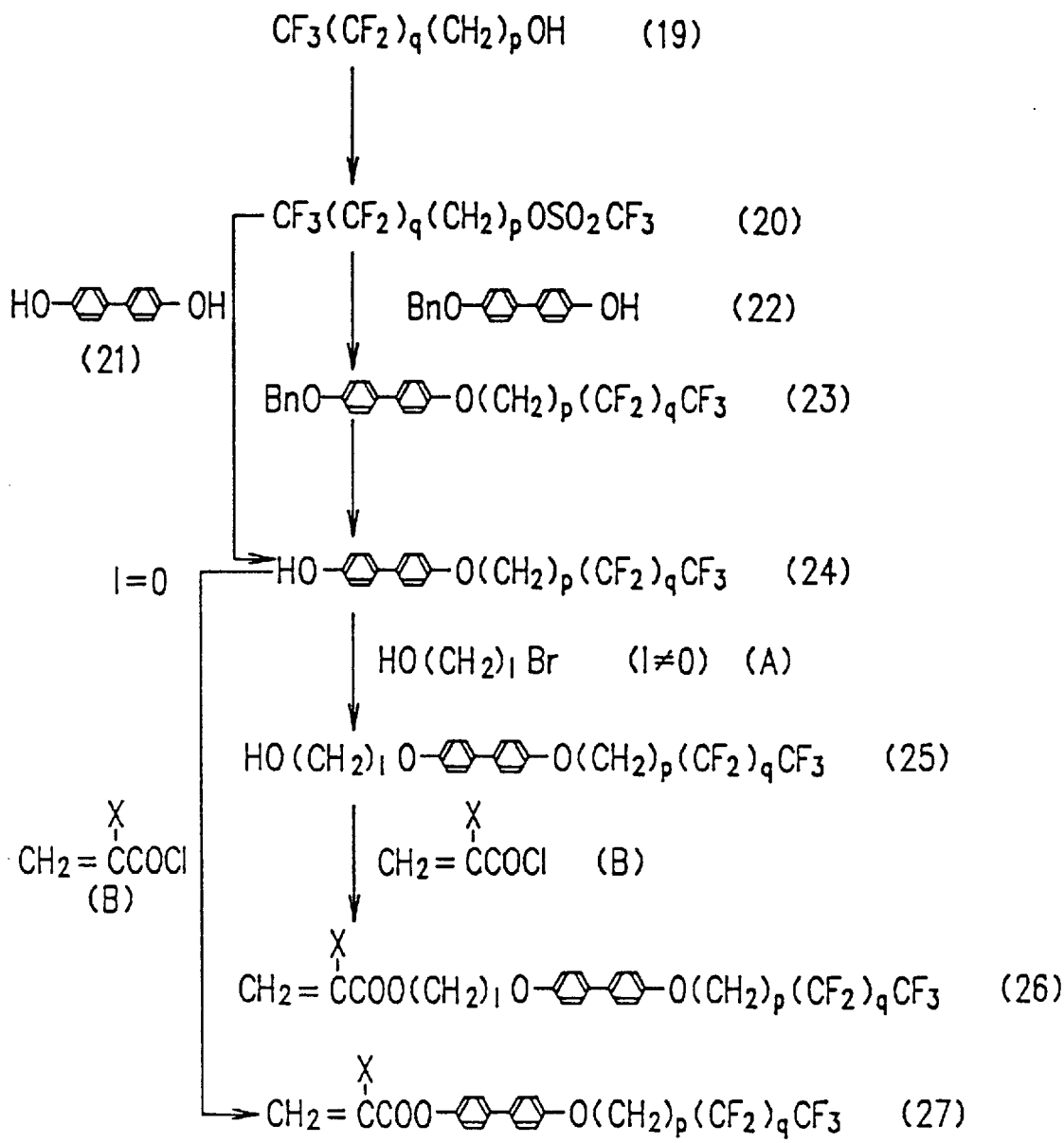
FIG. 3 is a reaction scheme diagram showing still another exemplary synthesis route of a polymerizable compound of the present invention.

Synthesis route 3 describes a case where n=1 and p≠0 in the above general Formula (I), with reference to the reaction scheme shown in FIG. 3.

First, trifluoromethanesulfonic anhydride is allowed to react with Compound (19) to obtain Compound (20). Thereafter, Compound (20) is etherified with Compound (22) to obtain Compound (23). Compound (23) is de-benzylated using hydrogen gas in the presence of a Pd catalyst to obtain Compound (24). Alternatively, Compound (24) can be obtained by etherifying Compound (20) with Compound (21).

Next, Compound (24) is etherified with Compound (A) to obtain Compound (25). Furthermore, Compound (25) is esterified with Compound (B) to obtain Compound (26), which is the target compound.

In the case where no linking group is present between the mesogen group and the ethylene-type unsaturated group (1=0), Compound (B) can be directly allowed to react with Compound (24) to obtain the target Compound (27).

Synthesis route 4

Figure 4:
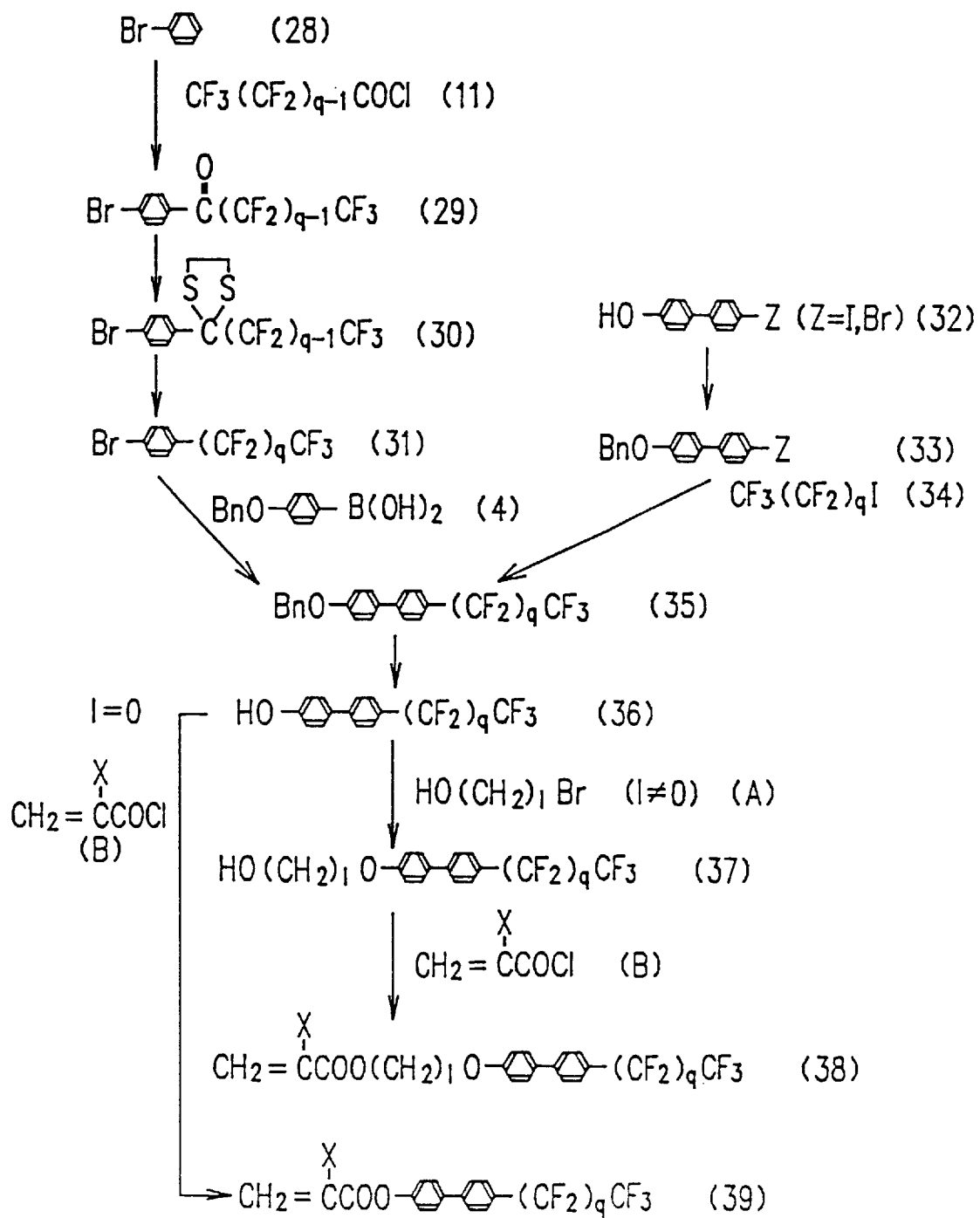
FIG. 4 is a reaction scheme diagram showing still another exemplary synthesis route of a polymerizable compound of the present invention.

Synthesis route 4 describes a case where n=0; p=0; and q≠0 in the above general Formula (I), with reference to the reaction scheme shown in FIG. 4.

First, Compound (28) and Compound (11) are allowed to have a Friedel Crafts reaction to obtain Compound (29). Thereafter, ethanedithiol is allowed to react with Compound (29) to obtain Compound (30).

Next, Compound (30) is fluorinated by using a hydrogen fluoride-pyridine solution to obtain Compound (31). Thereafter, Compound (31) and Compound (4) are allowed to have a coupling reaction in the presence of a Pd catalyst to obtain Compound (35). Alternatively, Compound (35) can be obtained by a coupling reaction between Compound (33) obtained by benzylating Compound (32) and Compound (34) in the presence of a Cu catalyst.

Finally, Compound (35) is de-benzylated using hydrogen gas in the presence of a Pd catalyst to obtain Compound (36). Thereafter, Compound (36) is etherified with Compound (A) to obtain Compound (37). Then, Compound (37) is esterified with Compound (B) to obtain Compound (38), which is the target compound.

In the case where no linking group is present between the mesogen group and the ethylene-type unsaturated group (1=0), Compound (B) can be directly allowed to react with Compound (36) to obtain the target Compound (39).

Synthesis route 5

Figure 5:
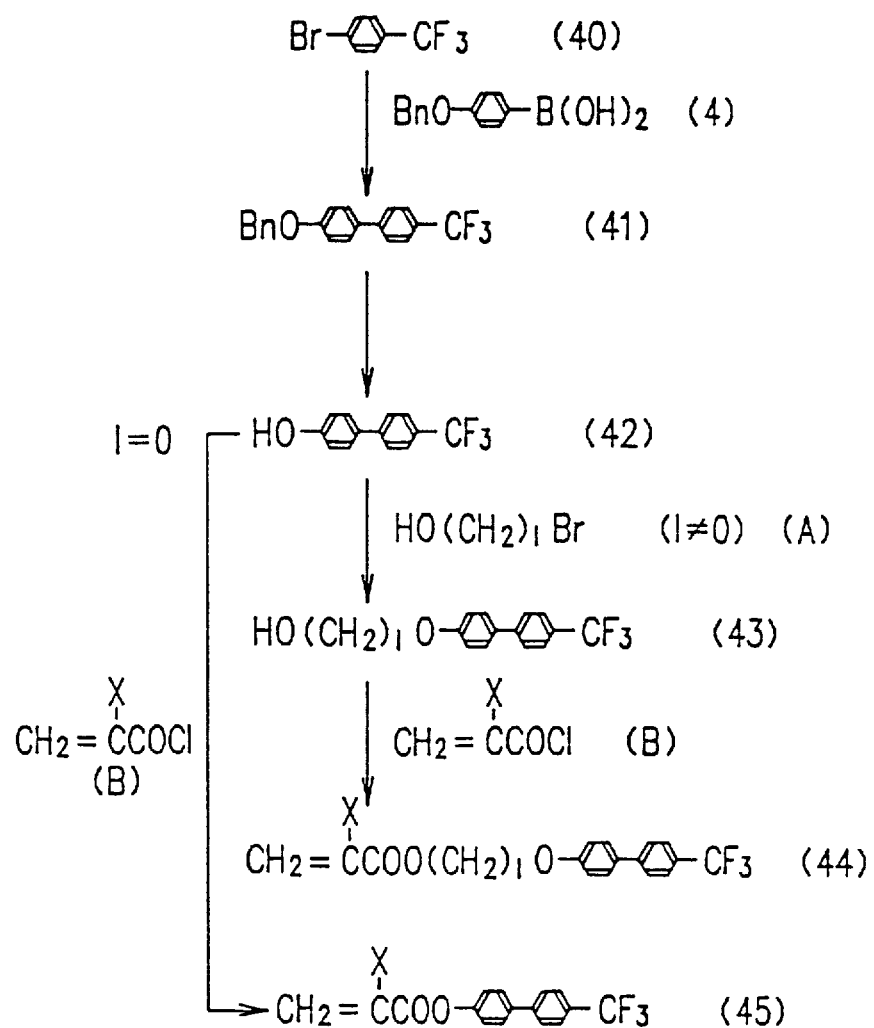
FIG. 5 is a reaction scheme diagram showing still another exemplary synthesis route of a polymerizable compound of the present invention.

Synthesis route 5 describes a case where n=p=q=0 in the above general Formula (I), with reference to the reaction scheme shown in FIG. 5.

First, Compound (40) and Compound (4) are allowed to have a coupling reaction in the presence of a Pd catalyst to obtain Compound (41). Thereafter, Compound (41) is de-benzylated using hydrogen gas in the presence of a Pd catalyst to obtain Compound (42). Compound (42) is etherified with Compound (A) to obtain Compound (43). Then, Compound (43) is allowed to react with Compound (B) to obtain Compound (44), which is the target compound.

In the case where no linking group is present between the mesogen group and the ethylene-type unsaturated group (1=0), Compound (B) can be directly allowed to react with Compound (42) to obtain the target Compound (45).

Synthesis route 6

Figure 6:
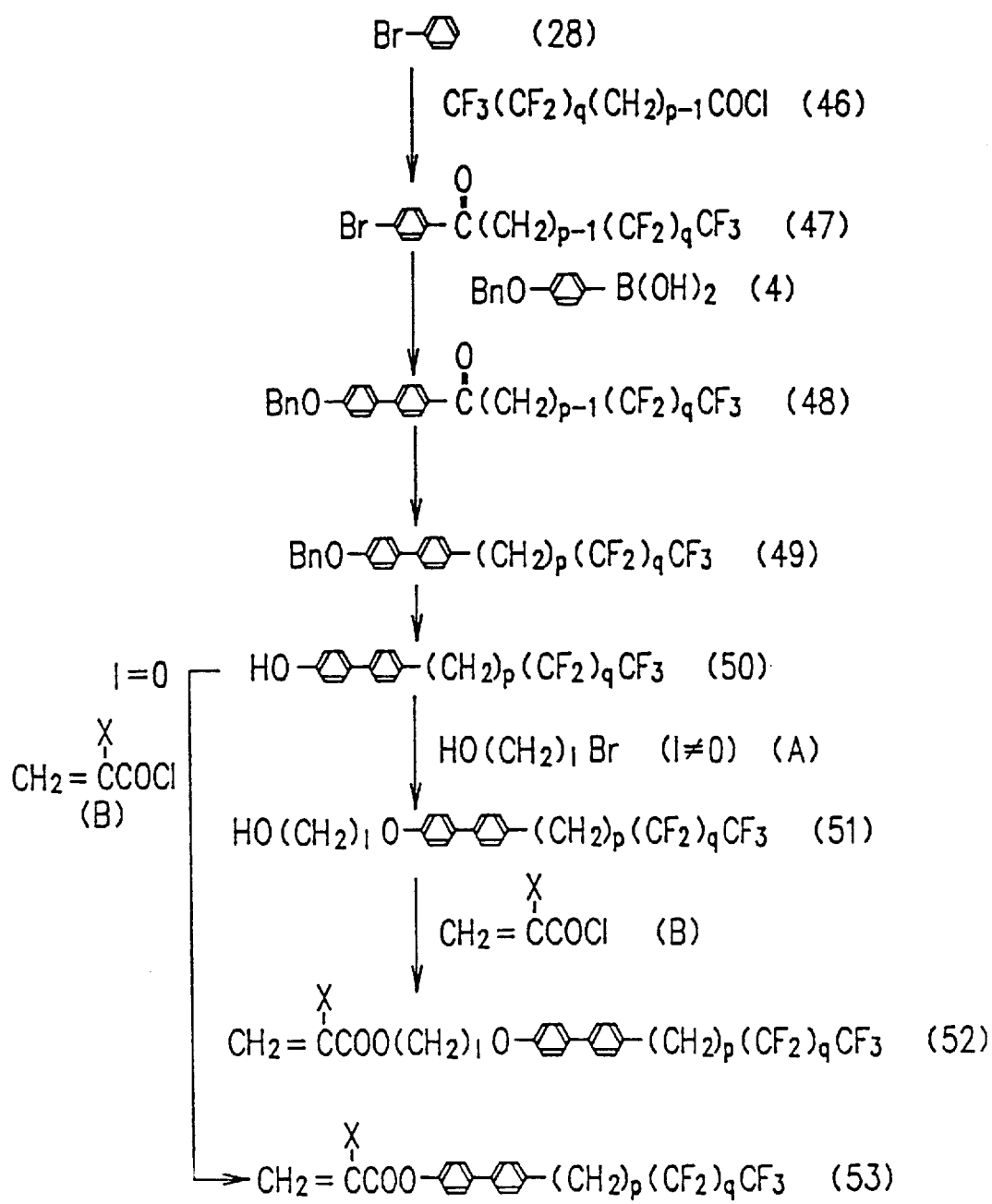
FIG. 6 is a reaction scheme diagram showing still another exemplary synthesis route of a polymerizable compound of the present invention.

Synthesis route 6 describes a case where n=0 and p≠0 in the above general Formula (I), with reference to the reaction scheme shown in FIG. 6.

First, Compound (28) and Compound (46) are allowed to have a Friedel Crafts reaction to obtain Compound (47). Thereafter, Compound (47) and Compound (4) are allowed to have a coupling reaction in the presence of a Pd catalyst to obtain Compound (48). Compound (48) is reduced to obtain Compound (49). Compound (49) is de-benzylated to obtain Compound (50).

Next, Compound (50) is etherified with Compound (A) to obtain Compound (51). Thereafter, Compound (51) is allowed to react with Compound (B) to obtain Compound (52), which is the target compound.

In the case where no linking group is present between the mesogen group and the ethylene-type unsaturated group (1=0), Compound (B) can be directly allowed to react with Compound (50) to obtain the target Compound (53).

The fluoroalkyl compounds to be used for the synthesis of the compounds of the present invention are either commercially available or derivable from commercially available compounds. For example, $C_kF_{2k+1}COOH$ (where k=1 to 10), $C_kF_{2k+1}I$ (where k=2, 3, 4, 6, 7, 8, or 10), $C_kF_{2k+1}CH_2OH$ (where k=1, 2, 3, 8, 9, or 10), $C_kF_{2k+1}CH_2CH_2OH$ (where k=4, 6, 8, or 10), and $C_kF_{2k+1}(CH_2)_6OH$ (where k=2, 4, 6, or 8) are commercially available from Daikin Fine Chemical Laboratory Ltd., PCR Inc., Aldrich Chemical Company, Inc., Fluorochem Ltd., and so on. Moreover, desired fluoroalkyl compounds can be derived by known methods such as carbon chain length extension, oxidation, reduction, or coupling reaction using these commercially available compounds as starting materials.

Liquid Crystal Display Device

The liquid crystal display device according to the present invention includes a pair of substrates, at least one of which is transparent, and a liquid crystal layer interposed between the pair of substrates, the liquid crystal layer including a polymer region and liquid crystal regions surrounded by the polymer region. The polymer region is formed from a monomer containing at least one kind of the present polymerizable compound.

The liquid crystal material to be used for the present invention can be any organic mixture exhibiting a liquid crystalline state in the vicinity of room temperature. Preferable liquid crystal materials are, although the present invention is not limited thereto, nematic liquid crystal (including liquid crystal for dual frequency driving and liquid crystal whose $\Delta\epsilon<0$), cholesteric liquid crystal (in particular those which have selective reflection characteristics in the visible spectrum), or smectic liquid crystal, ferroelectric liquid crystal, and discotic liquid crystal, for example. Among the above, nematic liquid crystal, cholesteric liquid crystal, and nematic liquid crystal with a chiral agent added thereto are particularly preferable because of their characteristics. In the case of nematic liquid crystal with a chiral agent added, the chiral agent is preferably added in such an amount that the liquid crystal has a helical pitch of 10 μm or more in terms of hysteresis, uniformity, coloration due to a d·Δn(phase difference), and the like. Moreover, those liquid crystal materials which have excellent resistance against chemical reactions are preferable, because of the photopolymerization performed during the process. Examples of such liquid crystal materials include those having a functional group such as fluorine atoms in the molecule, e.g., ZLI-4801-000, ZLI-4801-001, and ZLI-4792 (produced by MERCK KGaA). Two or more of the above liquid crystal materials can be mixed for use.

When any of the above liquid crystal materials is mixed with a monomer containing at least one kind of the present polymerizable compound, the mixing ratio of the liquid crystal material to the monomer (i.e., liquid crystal material: polymerizable compound) is preferably in the range of 97:3 to 60:40 by weight, and more preferably in the range of 90:10 to 70:30 by weight. If the monomer accounts for more than 40% by weight of the above-mentioned mixture, the liquid crystal regions capable of changing responsive to a voltage applied to electrodes of the liquid crystal device decrease, thereby often resulting in insufficient contrast. On the other hand, if the monomer accounts for less than 3% by weight of the above-mentioned mixture, the polymer region (typically a polymer wall) cannot be sufficiently formed, so that the liquid crystal display device may have insufficient pressure resistance and shock resistance, presenting a practicality problem.

The liquid crystal display device can be preferably produced as follows: First, a liquid crystal cell having transparent electrodes (thickness: 50 nm) of ITO (a complex of an indium oxide and a tin oxide) is formed. A photomask of a predetermined design is placed on the liquid crystal cell. Then, a homogenous mixture of a liquid crystal material and a monomer containing at least one kind of the present polymerizable compound is injected into the cell by capillary action. Thereafter, the cell is irradiated with UV rays through the photomask by means of a high-pressure mercury lamp capable of providing parallel light beams while applying a voltage between the transparent electrodes so as to cure the monomer. Thus, the liquid crystal display device is produced.

When a liquid crystal display device is produced using the present polymerizable compound as described above, it is likely that a region is created in the direction of 45° from the polarization axis of the polarizer that has poor viewing angle characteristics. The reasons are: 1) since the liquid crystal molecules are nearly upright with respect to the substrate ($\Delta\epsilon>0$) when a saturation voltage is applied, the polarizer has viewing angle characteristics; and (2) the liquid crystal layer has retardation of d·Δn. The cause of the above-described problem (2) is that light entering along the direction of the polarization axis of the polarizer has either an ordinary light component only or an extraordinary light component only when crossing the refractive index ellipsoid of the liquid crystal layer, but light entering in the direction of 45° from the polarization axis of the polarizer has both an ordinary light component and an extraordinary light component when crossing the refractive index ellipsoid of the liquid crystal layer (corresponding to a state where the polarization axes of two polarizers, disposed perpendicular to each other, seemingly constitute an angle larger than 90°). This causes significant leakage of light due to the generation of elliptic polarization. Therefore, it is preferable to minimize the retardation of the liquid crystal layer so as to prevent elliptic polarization. However, because the transmittance $T_0$ in the absence of a voltage is influenced by the retardation of the liquid crystal layer, it is preferable in terms of achieving omnidirectional viewing angle characteristics and brightness of the cell that the retardation of the liquid crystal layer be 300 nm to 650 nm. If the retardation is less than 300 nm, the cell shows a dark display due to the lack of brightness in the absence of a voltage. The twist angle is preferably 45° to 150°, and most preferably in the vicinity of 90°, at which the first minimum conditions are satisfied so that the highest brightness can be achieved.

Liquid crystal molecules have excellent orientability when forming a liquid crystal device using the present polymerizable compound. However, the orientation of liquid crystal molecules can be further controlled by using various alignment techniques. Examples of alignment techniques suitably used for the present invention include: a rubbing method where a substrate of the liquid crystal cell is rubbed with cloth after applying a polymer material such as polyimide or an inorganic material on the substrate; vertical orientation method where a compound having a small surface tension is applied onto the substrate; oblique orientation method where $SiO_2$ or the like is obliquely vapor-deposited; and a horizontal alignment film method where no rubbing treatment is conducted. Alternatively an unprocessed substrate (i.e., a substrate merely provided with transparent electrodes) can also be used.

As for materials of the substrates of the liquid crystal display device of the present invention, those which are made from transparent solids, e.g., glass plates or plastic plates (such as polymer films), and those which are made from opaque solids, e.g., substrates with a thin metal film or Si substrates, can be suitably used. Substrates with a thin metal film are effective for a reflection type liquid crystal display device.

When using plastic, the substrate is preferably made from a material which does not absorb visible light, e.g., PET, acrylic polymers, polystyrene, polycarbonate, and the like. By using plastic substrates, the substrates themselves may be provided with some polarization ability.

Moreover, a laminated substrate combining two different types of substrates, or a laminated substrate made by combining two substrates of either the same or different types having different thicknesses can also be used.

In the case where the liquid crystal display device produced in the above-described manner is further subjected to the above-described liquid crystal alignment techniques such as rubbing or $SiO_2$ oblique deposition, it is possible to sandwich the liquid crystal display device with two polarizers to obtain a liquid crystal device in which any conventional orientation-controlled display mode having a high contrast and steep driving voltage characteristics (e.g., TN, STN, ECB, and SSFLC) is accommodated as well as a liquid crystal layer including liquid crystal regions surrounded by polymer regions.

Liquid crystal molecules in the liquid crystal regions of a liquid crystal display device thus produced can take any orientation state. Typical examples of the orientation states include: an axially-symmetrical orientation, a radial orientation, concentric orientation, a random orientation, or a spiral orientation.

The liquid crystal device thus formed, or a liquid crystal device formed by sandwiching the above liquid crystal device with two polarizers can be driven by a driving method such as simple matrix driving and active driving method, e.g., a-Si TFT, p-Si TFT, and MIM. However, the present invention does not provide any limitation as to the driving method.

Since the present polymerizable compound includes a mesogen backbone in its molecule, a mesogen backbone is introduced in a polymer formed from a monomer containing the present polymerizable compound. The present polymerizable compound, including a mesogen backbone, provides the following effects:

When a liquid crystal display device of a display mode utilizing orientation restricting force of a substrate (which is substantially provided by an alignment film formed thereon) is produced by using a liquid crystal material and a polymerizable compound, a polymer region formed from the polymerizable compound is formed between the alignment and a liquid crystal region, thereby reducing the orientation restriction force of the alignment film for the liquid crystal molecules. On the other hand, when a mesogen backbone is introduced in the molecule of the polymerizable compound, as in the present polymerizable compound, polymer having a structure similar to that of liquid crystal molecules exists in the polymer region. As a result, the polymer region becomes capable of transmitting the orientation restricting force of the alignment film. Therefore, even if such a polymer region exists between the liquid crystal region and the alignment film, the orientation restricting force of the alignment film is sufficiently transmitted to the liquid crystal molecules within the liquid crystal regions, whereby the orientation state of liquid crystal molecules within the liquid crystal regions is stabilized.

Moreover, the present polymerizable compound includes a fluorinated alkyl group of a specific size at one end of the molecule.

Since the fluorinated portion has a different level of surface free energy than that of non-fluorinated portions, the fluorinated portion emerges on the surface of the polymer region. As a result, the surface free energy of the polymer region surface decreases so as to decrease the anchoring strength of liquid crystals, whereby the orientation state of the liquid crystal is stabilized. Moreover, the fluorinated portion has a different level of surface free energy than that of the liquid crystal material, the compatibility between the polymer material and the liquid crystal material decreases. As a result, the response time of the liquid crystal decreases, thereby improving the threshold characteristics of voltage-transmittance characteristics and the steepness of voltage response. Furthermore, since the fluorinated alkyl group is introduced at an end of the molecule of the present polymerizable compound, the anchoring strength and the compatibility between the polymer material and the liquid crystal material further decrease (thereby enabling even faster response and improving the threshold characteristics of voltage-transmittance characteristics and the steepness of voltage response). The reason is that, relative to a fluorinated alkyl group introduced at the central portion of the polymerizable compound or the mesogen backbone, the fluorinated alkyl group introduced at an end of the molecule can more easily move to the surface of the polymer region. Moreover, a larger amount of fluorine can be introduced at an end of the molecule than in the central portion or the mesogen backbone of the molecule.

Figure 15:
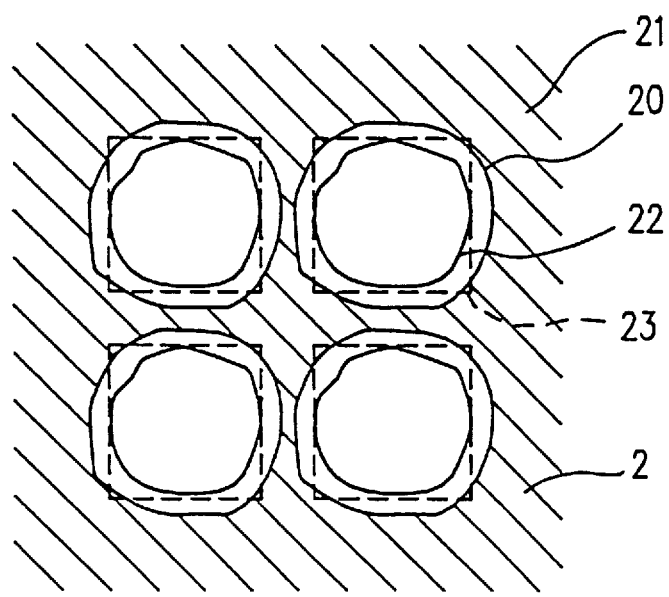
FIG. 15 is a schematic view describing disclination lines occurring when a voltage is applied.

In most conventional liquid crystal display devices including liquid crystal regions in which liquid crystal molecules are oriented symmetrically with respect to an axis (vertical to the substrate surface), disclination lines occur in the periphery of liquid crystal regions due to a reverse tilt phenomenon (see FIG. 15). However, the use of the present polyinerizable compound minimizes the generation of such disclination lines when a voltage is applied, which would otherwise degrade the black display level, because the present polymerizable compound causes the liquid crystal molecules to have a pretilt.

Thus, the display characteristics (viewing angle characteristics, contrast, response time, threshold characteristics and steepness) of a liquid crystal display device using the present polymerizable compound can drastically improve.

As well as studying the effects provided by the use of the present polymerizable compound, the inventors of the present invention also studied methods for combining the present polymerizable compound with a liquid crystal material in such a manner that the size of liquid crystal droplets (liquid crystal regions) surrounded by a polymer region substantially equals the size of pixels and that substantially one liquid crystal droplet is regularly disposed corresponding to each pixel. As a result of the study, the inventors found the following two methods to be very effective:

(A) a method in which UV rays are radiated having a spatial regularity having portions with varying levels of high and low, the portions having substantially the same size as that of the diameter of liquid crystal droplets and therefore the size of pixels (i.e., UV rays are selectively radiated by being partially intercepted in regions substantially corresponding to pixels) so as to form a liquid crystal display device having a liquid crystal layer including liquid crystal regions surrounded by a polymer region; and (B) a method in which the surface free energy of the substrates is controlled in patterns for forming a liquid crystal display device having a liquid crystal layer including liquid crystal regions surrounded by a polymer region (e.g., a method in which a material having different levels of surface free energy for the liquid crystal phase (e.g., liquid crystal material) and the isotropic phase (e.g., polymer material) is previously patterned onto a substrate to form a surface pattern which is utilized in disposing a liquid crystal material on the substrate).

EXAMPLES

The following are illustrative examples of the present invention. However, the present invention is not intended to be limited to these examples.

The abbreviations used in the following examples represent the following items.

GC: gas chromatography
HPLC: high-performance liquid chromatography
TLC: thin layer chromatography
IR: infrared absorption spectrum
Mass: mass spectrum
b.p.: boiling point
m.p.: melting point
Y: yield
C: crystal
SA: smectic A phase
Sx: unidentifiable smectic phase
Ne: nematic phase
Iso: isotropic liquid
?: uncertain, unidentified temperature Example 1

A polymerizable compound according to the present invention, which is represented by the following Formula (II), was synthesized.

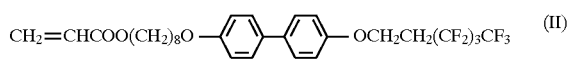

Hereinafter, the synthesis procedure of the above compound is described.

(a) Synthesis of $CF_3(CF_2)_3CH_2CH_2OSO_2CF_3$:

In a flask whose content had been replaced with Ar, 66.0 g of 2-(perfluorobutyl)ethanol and 180 ml of methylene chloride were placed. To this solution, 88.3 g of trifluoromethanesulfonic anhydride and then 31.7 g of triethylamine were added dropwise at 5° C. or less. The reaction solution was allowed to warm up to room temperature, and was stirred overnight. Thereafter, the reaction solution was washed with 75 ml of water, 75 ml of 3% dilute sulfuric acid, and 75 ml of water in this order, and the solvent was distilled away. The residue was distilled under a reduced pressure to give 88.3 g of 2-(perfluorobutyl)ethyl trifluoromethane sulfonate (Y: 92%). The purity of the compound thus obtained was 94% by GC, and its b.p. was 88° C. to 90° C./28 mmHg.

(b) Synthesis of a compound represented by Formula (III):

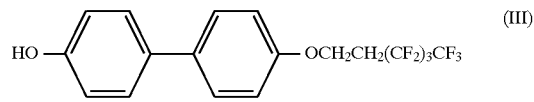

In a Schlenk tube whose content had been replaced with Ar, 9.0 g of 60% sodium hydride and 400 ml of dry dimethoxyethane were placed. While this solution was being cooled with ice water, 29.8 g of 4,4'-dihydroxybiphenyl was added. Thereafter, the reaction solution was allowed to warm up to room temperature, and was stirred for two hours. Thereafter, the reaction solution was cooled to −60° C. After 86 g of 2-(perfluorobutyl)ethyl trifluoromethane sulfonate was added dropwise to the reaction solution, the reaction solution was allowed to warm up to room temperature, and was stirred overnight. Subsequently, the reaction solution was poured into dilute hydrochloric acid, and an organic layer was extracted with benzene. After the benzene layer was washed with water and dried over sodium sulfate anhydrous, the solvent was distilled away. The residue was purified by silica gel column chromatography (eluent: benzene), and recrystallized from toluene to give 18.8 g of 4-hydroxy-4'-[2-(perfluorobutyl)ethyloxy]biphenyl (Y: 27.1%). The purity of the compound thus obtained was 98.4% by GC.

(c) Synthesis of a compound represented by Formula (IV):

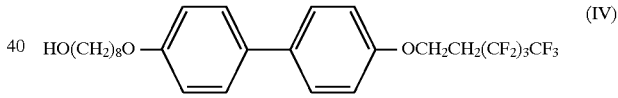

In a flask, 1.7 g of 4-hydroxy-4'-[2-(perfluorobutyl) ethyloxy]biphenyl and 10 ml of tetrahydrofuran were placed. To this solution, 3.9 ml of a 1N aqueous solution of potassium hydroxide was added and stirred for a while. After the solvent was distilled away under a reduced pressure, 15 ml of methanol and 0.85 g of 8-bromooctanol were added to the solution and stirred under reflux for 12 hours. Next, the reaction solution was poured into water, and an organic layer was extracted with ether. The ether layer was washed with dilute hydrochloric acid and water in this order. After the solvent was distilled away, the residue was purified by silica gel column chromatography (eluent: benzene/ethyl acetate= 9/1), and recrystallized from toluene to give 1.5 g of 4-(8-hydroxyoctyloxy)-4'-[2-(perfluorobutyl)ethyloxy] biphenyl (Y: 67.2%). The purity of the compound thus obtained was 98.8% by GC.

(d) Synthesis of the compound represented by Formula (II):

In a flask whose content had been replaced with Ar, 1.5 g of 4-(8-hydroxyoctyloxy)-4'-[2-(perfluorobutyl)ethyloxy] biphenyl, 0.3 g of triethylamine, and 16 ml of tetrahydrofuran were placed. While this solution was being cooled with ice water, 0.3 g of acryloyl chloride was added dropwise. The reaction solution was allowed to warm up to room temperature, and was stirred for 3 hours. Thereafter, the reaction solution was poured into water and an organic layer was extracted with benzene. After the benzene layer was washed with water and dried over sodium sulfate anhydrous, the solvent was distilled away. The residue was purified by silica gel column chromatography (eluent: benzene), and recrystallized from acetone to give 0.7 g of 4-[8-(acryloyloxy)octyloxy]-4'-[2-(perfluorobutyl)ethyloxy]biphenyl (Y: 44.4%). The purity of the compound thus obtained was 98.4% by GC; 99.4% by HPLC; and 1 spot by TLC. The phase transition temperature of the resultant compound was as shown in Table 2 below.

TABLE 2

Phase transition temperature: C $\xrightarrow{82.8° C.}$ Sa $\xrightarrow{90.8° C.}$ Iso The resultant material was confirmed to be the compound represented by Formula (II), based on an IR measurement, Mass analysis which revealed a molecular ion peak at 614, and the information of the materials used.

Example 2

A polymerizable compound according to the present invention, which is represented by the following Formula (V), was synthesized.

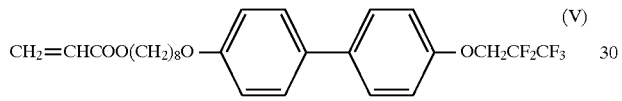

Hereinafter, the synthesis procedure of the above compound is described.

(a) Synthesis of $CF_3CF_2CH_2OSO_2CF_3$:

By the same synthesis procedure as in (a) of Example 1 except for using 37.5 g of 2,2,3,3,3-pentafluoropropanol instead of 66.0 g of 2-(perfluorobutyl)ethanol, 64.0 g of 2,2,3,3,3-pentafluoropropyl trifluoromethane sulfonate (Y: 90.7%) was obtained. The b.p. of the resultant compound was 97° C. to 98° C.

(b) Synthesis of a compound represented by Formula (VI):

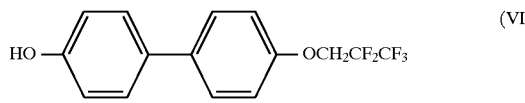

By the same synthesis procedure as in (b) of Example 1 except for using 63.2 g of 2,2,3,3,3-pentafluoropropyl trifluoromethane sulfonate instead of 86 g of 2-(perfluorobutyl)ethyl trifluoromethane sulfonate, 24.9 g of 4-hydroxy-4'-(2,2,3,3,3-pentafluoropropyloxy)biphenyl (Y: 35.0%) was obtained.

The purity of the resultant compound was 98.8% by GC. (c) Synthesis of a compound represented by Formula (VII):

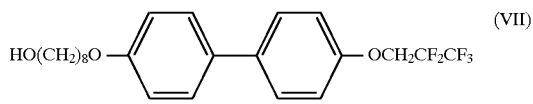

By the same synthesis procedure as in (c) of Example 1 except for using 1.24 g of 4-hydroxy-4'-(2,2,3,3,3-pentafluoropropyloxy)biphenyl instead of 1.7 g of 4-hydroxy-4'-[2-(perfluorobutyl)ethyloxy]biphenyl, 1.1 g of 4-(8-hydroxyoctyloxy)-4'-(2,2,3,3,3-pentafluoropropyloxy)biphenyl (Y: 64.2%) was obtained.

(d) Synthesis of a compound represented by Formula (V):

By the same synthesis procedure as in (d) of Example 1 except for using 1.1 g of 4-(8-hydroxyoctyloxy)-4'- 2,2,3,3,3-pentafluoropropyloxy)biphenyl instead of 1.5 g of 4-(8-hydroxyoctyloxy)-4'-[2-(perfluorobutyl)ethyloxy]biphenyl, 0.5 g of 4-[8-(acryloyloxy)octyloxy]-4'-(2,2,3,3,3-pentafluoropropyloxy)biphenyl (Y: 40.6%) was obtained. The m.p. of the resultant compound was 73.7° C. The purity of the resultant compound was 98.2% by GC; 98.0% by HPLC; and 1 spot by TLC.

The resultant material was confirmed to be the compound represented by Formula (V), based on an IR measurement, Mass analysis which revealed a molecular ion peak at 500, and the information of the materials used.

Example 3

A polymerizable compound according to the present invention, which is represented by the following Formula (VIII), was synthesized.

Hereinafter, the synthesis procedure of the above compound is described.

(a) Synthesis of a compound represented by the following Formula (IX):

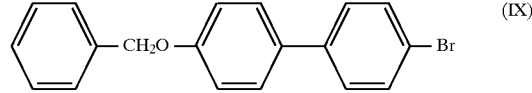

In a flask, 25 g of benzyl bromide, 36.4 g of 4-bromo-4'-hydroxybiphenyl, 40.4 g of potassium carbonate, and 300 ml of 2-butanone were placed, and stirred under reflux for 6 hours. The reaction solution was poured into water, and an organic layer was extracted with toluene. After the toluene layer was washed with water and dried over sodium sulfate anhydrous, the solvent was distilled away. The residue was recrystallized from acetone to give 42.5 g of 4-bromo-4'-benzyloxybiphenyl (Y: 85.8%). The purity of the compound thus obtained was 99.0% by GC.

(b) Synthesis of a compound represented by Formula (X):

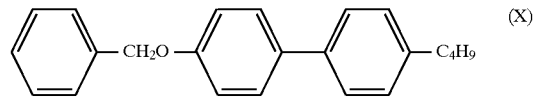

In a flask whose content had been replaced with Ar, 13.5 g of 4-bromo-4'-benzyloxybiphenyl, 12.6 g of Cu powder, and 40 ml of anhydrous dimethylsulfoxide were placed. After 15.2 g of perfluorobutyl iodide was added dropwise to this solution at 60° C., the solution was stirred for 2 hours at 60° C., and 4 hours at 110° C. After the reaction solution was allowed to cool down, chloroform was added into the reaction solution. After the undissolved content was removed by filtration, the filtrate was washed with water and dried over sodium sulfate anhydrous. After the solvent was distilled away, the residue was purified by silica gel column chromatography (eluent: hexane/toluene=6/1), and recrystallized from acetone to give 17.1 g of 4-perfluorobutyl-4'-benzyloxybiphenyl (Y: 89.8%). The purity of the compound thus obtained was 96.2% by GC, and its m.p. was 128° C. to 134° C.

(c) Synthesis of a compound represented by Formula (XI):

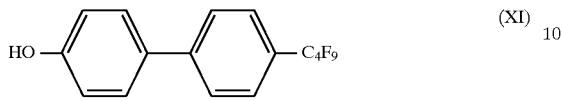

In an autoclave, 16.6 g of 4-perfluorobutyl-4'-benzyloxybiphenyl, 1 g of 10% palladium-carbon, and 110 ml of tetrahydrofuran were placed, and stirred in a hydrogen atmosphere under pressure for 24 hours. After the reaction solution was filtrated to remove the catalyst, the filtrate was concentrated and the residue was recrystallized from acetone to give 9.4 g of 4perfluorobutyl-4'-hydroxybiphenyl (Y: 69.8%). The purity of the compound thus obtained was 98.3% by GC, and its m.p. was 131° C. to 134° C.

(d) Synthesis of a compound represented.by Formula (XII):

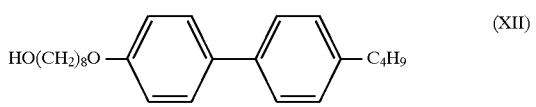

In a flask, 8 g of 4-perfluorobutyl-4'-hydroxybiphenyl, 50 ml of tetrahydrofuran, and 25 ml of a 1N aqueous solution of potassium hydroxide were placed and stirred for a while. After the solvent was distilled away, 5.3 g of 8-bromooctanol and 60 ml of methanol were added to the solution and stirred under reflux for 15 hours. Next, the reaction solution was poured into water, and an organic layer was extracted with toluene. The toluene layer was washed with water, and dried over sodium sulfate anhydrous. After the solvent was distilled away, the residue was purified by silica gel column chromatography (eluent: toluene/ethyl acetate=12/1), and recrystallized from acetone to give 4.5 g of 4-perfluorobutyl-4'-(8-hydroxyoctyl)oxybiphenyl (Y: 42.3%). The purity of the compound thus obtained was 92.2% by GC, and its m.p. was 102° C. to 104° C.

(e) Synthesis of the compound represented by Formula (VIII):

In a flask, 4.1 g of 4-perfluorobutyl-4'-(8-hydroxyoctyl)oxybiphenyl, 0.9 g of triethylamine, and 40 ml of tetrahydrofuran were placed. While this solution was being cooled with ice water, 0.8 g of acryloyl chloride was added dropwise. The reaction solution was allowed to warm up to room temperature and was stirred for 2 hours. Thereafter, the reaction solution was poured into water, and an organic layer was extracted with benzene. The benzene layer was washed with water, and dried over sodium sulfate anhydrous. After the solvent was distilled away, the residue was purified by silica gel column chromatography (eluent: benzene), and recrystallized from hexane to give 2.6 g of 4-[8-(acryloyloxy)octyloxy]-4'-perfluorobutylbiphenyl (Y: 57.7%). The m.p. of the compound thus obtained was 45.0° C. The purity of the compound thus obtained was 99.8% by GC; 99.9% by HPLC; and 1 spot by TLC.

The resultant material was confirmed to be the compound represented by Formula (VIII), based on an IR measurement, Mass analysis which revealed a molecular ion peak at 570, and the information of the materials used.

Example 4

A polymerizable compound according to the present invention, which is represented by the following Formula (XIII), was synthesized.

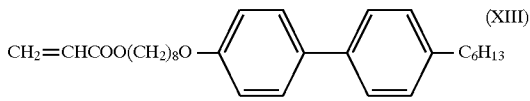

Hereinafter, the synthesis procedure of the above compound is described.

(a) Synthesis of a compound represented by the following Formula (XIV):

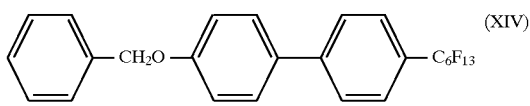

By the same synthesis procedure as in (b) of Example 3 except for using 19.6 g of perfluorohexyl iodide instead of 15.2 g of perfluorobutyl iodide, 12.8 g of 4-perfluorohexyl-4'-benzyloxybiphenyl (Y: 50.4%) was obtained. The m.p. of the resultant compound was 137° C. to 143° C.

(b) Synthesis of a compound represented by Formula (XV):

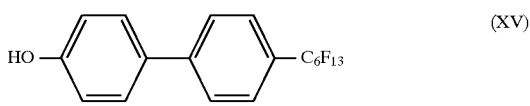

By the same synthesis procedure as in (c) of Example 3 except for using 12.5 g of 4-perfluorohexyl-4"-benzyloxybiphenyl instead of 16.6 g of 4-perfluorobutyl-4"-benzyloxybiphenyl, 10.0 g of 4-perfluorohexyl-4"-hydroxybiphenyl (Y: 94.9%) was obtained. The purity of the resultant compound was 98.5% by GC, and its m.p. was 142° C. to 147° C.

(c) Synthesis of a compound represented by Formula (XVI):

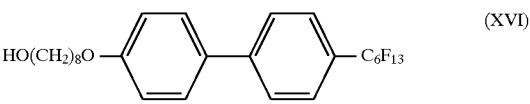

By the same synthesis procedure as in (d) of Example 3 except for using 10 g of 4-perfluorohexyl-4'-hydroxybiphenyl instead of 8 g of 4-perfluorobutyl-4'-hydroxybiphenyl, 6.3 g of 4-perfluorohexyl-4'-(8-hydroxyoctyl)oxybiphenyl (Y: 49.9%) was obtained. The purity of the resultant compound was 95.4% by GC.

(d) Synthesis of the compound represented by Formula (XIII):

By the same synthesis procedure as in (e) of Example 3 except for using 4.9 g of 4-perfluorohexyl-4'-(8-hydroxyoctyl)oxybiphenyl instead of 4.1 g of 4-perfluorobutyl-4'-(8-hydroxyoctyl)oxybiphenyl, 3.3 g of 4-[8-(acryloyloxy)octyloxy]-4'-perfluorohexylbiphenyl (Y: 62%) was obtained. The m.p. of the resultant compound was 54.3° C. The purity of the resultant compound was 99.3% by GC; 99.5% by HPLC; and 1 spot by TLC.

The resultant material was confirmed to be the compound represented by Formula (XIII), based on an IR measurement, Mass analysis which revealed a molecular ion peak at 670, and the information of the materials used.

Example 5

A polymerizable compound according to the present invention, which is represented by the following Formula (XVII), was synthesized.

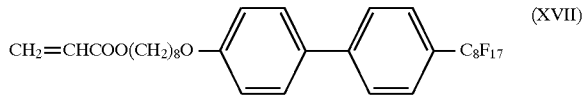

Hereinafter, the synthesis procedure of the above compound is described.

(a) Synthesis of a compound represented by the following Formula (XVIII):

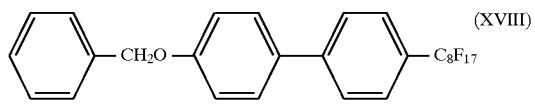

By the same synthesis procedure as in (b) of Example 3 except for using 24.0 g of perfluorooctyl iodide instead of 15.2 g of perfluorobutyl iodide, 16.1 g of 4-perfluorooctyl-4'-benzyloxybiphenyl (Y: 54.0%) was obtained. The purity of the resultant compound was 97.6% by GC.

(b) Synthesis of a compound represented by Formula (XIX):

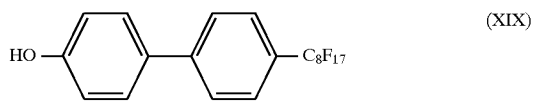

By the same synthesis procedure as in (c) of Example 3 except for using 16.0 g of 4-perfluorooctyl-4'-benzyloxybiphenyl instead of 16.6 g of 4-perfluorobutyl-4'-benzyloxybiphenyl, 12.7 g of 4-perfluorooctyl-4'-hydroxybiphenyl (Y: 92%) was obtained. The purity of the resultant compound was 97.6% by GC, and its m.p. was 162.5° C. to 164.5° C.

(c) Synthesis of a compound represented by Formula (XX):

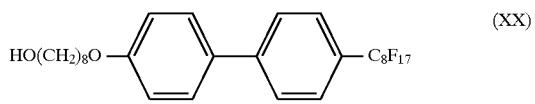

By the same synthesis procedure as in (d) of Example 3 except for using 12.1 g of 4-perfluorooctyl-4'-hydroxybiphenyl instead of 8 g of 4-perfluorobutyl-4'-hydroxybiphenyl, 5.9 g of 4-perfluorooctyl-4'-(8-hydroxyoctyl)oxybiphenyl (Y: 40.1%) was obtained. The purity of the resultant compound was 98% by GC.

(d) Synthesis of the compound represented by Formula (XVII):

By the same synthesis procedure as in (e) of Example 3 except for using 5.7 g of 4-perfluorooctyl-4'-(8-hydroxyoctyl)oxybiphenyl instead of 4.1 g of 4-perfluorobutyl-4'-(8-hydroxyoctyl)oxybiphenyl, 1.6 g of 4-[8-(acryloyloxy)octyloxy]-4'-perfluorooctylbiphenyl (Y: 26%) was obtained. The m.p. of the resultant compound was 75.5° C. The purity of the resultant compound was 98.2% by GC; 99.0% by HPLC; and 1 spot by TLC.

The resultant material was confirmed to be the compound represented by Formula (XVII), based on an IR measurement, Mass analysis which revealed a molecular ion peak at 770, and the information of the materials used.

Example 6

A polymerizable compound according to the present invention, which is represented by the following Formula (XXI), was synthesized.

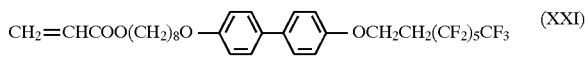

Hereinafter, the synthesis procedure of the above compound is described.

(a) Synthesis of $CF_3(CF_2)_5CH_2CH_2OSO_2CF_3$:

By the same synthesis procedure as in (a) of Example 1 except for using 91 g of 2-(perfluorohexyl)ethanol instead of 66.0 g of 2-(perfluorobutyl)ethanol, 98.9 g of 2-(perfluorohexyl)ethyl trifluoromethane sulfonate (Y: 80%). The b.p. of the compound thus obtained was 64° C./0.7 mmHg.

(b) Synthesis of a compound represented by Formula (XXII):

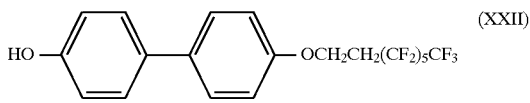

By the same synthesis procedure as in (b) of Example 1 except for using 107.6 g of 2-(perfluorohexyl)ethyl trifluoromethane sulfonate instead of 86 g of 2-(perfluorobutyl)ethyl trifluoromethane sulfonate, 35.7 g of 4-hydroxy-4'-[2-(perfluorohexyl)ethyloxy]biphenyl (Y: 31%) was obtained. The purity of the resultant compound was 99.7% by GC, and its phase transition temperature was as shown in Table 3 below:

TABLE 3

Phase transition temperature: $C \xrightarrow{80°C.} Sx \xrightarrow{170°C.} Ne \xrightarrow{181°C.} Iso$ (c) Synthesis of a compound represented by Formula (XXIII):

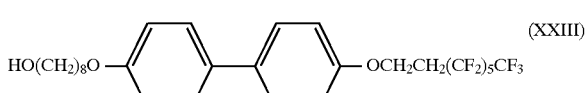

By the same synthesis procedure as in (c) of Example 1 except for using 2.1 g of 4-hydroxy-4'-[2-(perfluorohexyl)ethyloxy]biphenyl instead of 1.7 g of 4-hydroxy-4'-[2-(perfluorobutyl)ethyloxy]biphenyl, 2.0 g of 4-(8-hydroxyoctyloxy)-4'-[2-(perfluorohexyl)ethyloxy]biphenyl (Y: 78%) was obtained. The purity of the resultant compound was 74.8% by GC, and its phase transition temperature was as shown in Table 4 below:

TABLE 4

Phase transition temperature: $C \xrightarrow{?} Sx \xrightarrow{155°C.} Ne \xrightarrow{159°C.} Iso$ (d) Synthesis of the compound represented by Formula (XXI):

By the same synthesis procedure as in (d) of Example 1 except for using 1.76 g of 4-(8-hydroxyoctyloxy)-4'-[2-(perfluorohexyl)ethyloxy]biphenyl instead of 1.5 g of 4-(8-hydroxyoctyloxy)-4'-[2-(perfluorobutyl)ethyloxy]biphenyl, 1.1 g of 4-[8-(acryloyloxy)octyloxy]-4'-[2-(perfluorohexyl) ethyloxy]biphenyl (Y: 58%) was obtained. The phase transition temperature of the resultant compound was as shown in Table 5 below:

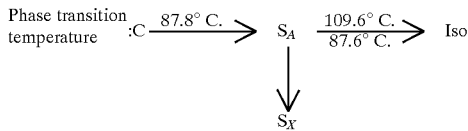

The purity of the resultant compound was 99.9% by GC; 99.9% by HPLC; and 1 spot by TLC.

The resultant material was confirmed to be the compound represented by Formula (XXI), based on an IR measurement, Mass analysis which revealed a molecular ion peak at 714, and the information of the materials used.

Examples 7–10

Liquid crystal display devices (Examples 7–10) were produced using the above-described present polymerizable compound by mask pattern exposition. Hereinafter, the method of production thereof will be described.

Figure 7:
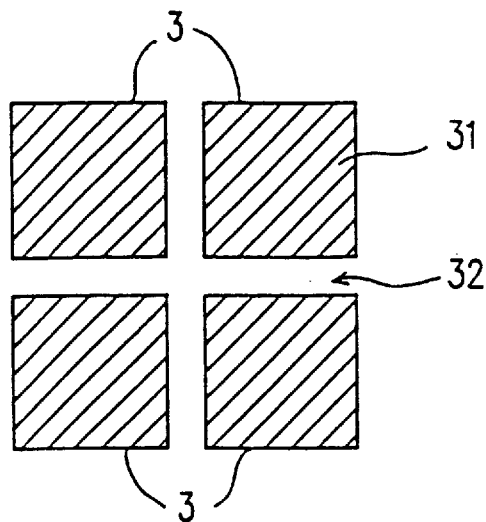
FIG. 7 is a conceptual view showing a photomask used in an example of the present invention.

A cell was constructed by using two glass substrates (thickness: 1.1 mm) having transparent electrodes of ITO (thickness: 50 nm) formed thereon and spacers (average particle diameter: 5 μm) for securing a cell thickness. A photomask 3 having shading portions 31 and light transmitting portions 32 as shown in FIG. 7 was placed on one face of the cell thus fabricated. The shading portions 31 were formed so as to correspond to pixels.

Furthermore, a mixture was prepared by homogeneously mixing the following substances: a resin composition containing 0.65 g of isobornyl acrylate, 0.15 g of 1,4-butanediolacrylate, 0.10 g of p-phenylstyrene, and 0.10 g of polymerizable compound X shown in Table 6 below; a liquid crystal material containing 13.3 g of ZLI-4792 (manufactured by MERCK KGaA; Δn=0.094); and a photopolymerization initiator consisting of 0.04 g of Irgacure 651 (manufactured by CIBA-GEIGY Corporation). The homogenous mixture was injected into the cell through capillary action to form a liquid crystal cell.

Thereafter, the cell was irradiated with UV rays at 100° C. for 8 minutes through the photomask under a high-pressure mercury lamp (capable of providing collimated light) where a power of 10 mW/cm² was obtained, while a voltage of ±4 V was applied between the transparent electrodes. Thus, the UV rays were radiated onto the cell in a pattern having a spatial regularity.

Thereafter, while continually applying the voltage, the cell was gradually (at a rate of 10° C./hr) cooled to 25° C. (where liquid crystal takes a nematic state), and the cell was further irradiated with UV rays for 3 consecutive minutes so as to cure the resin composition.

Figure 8:
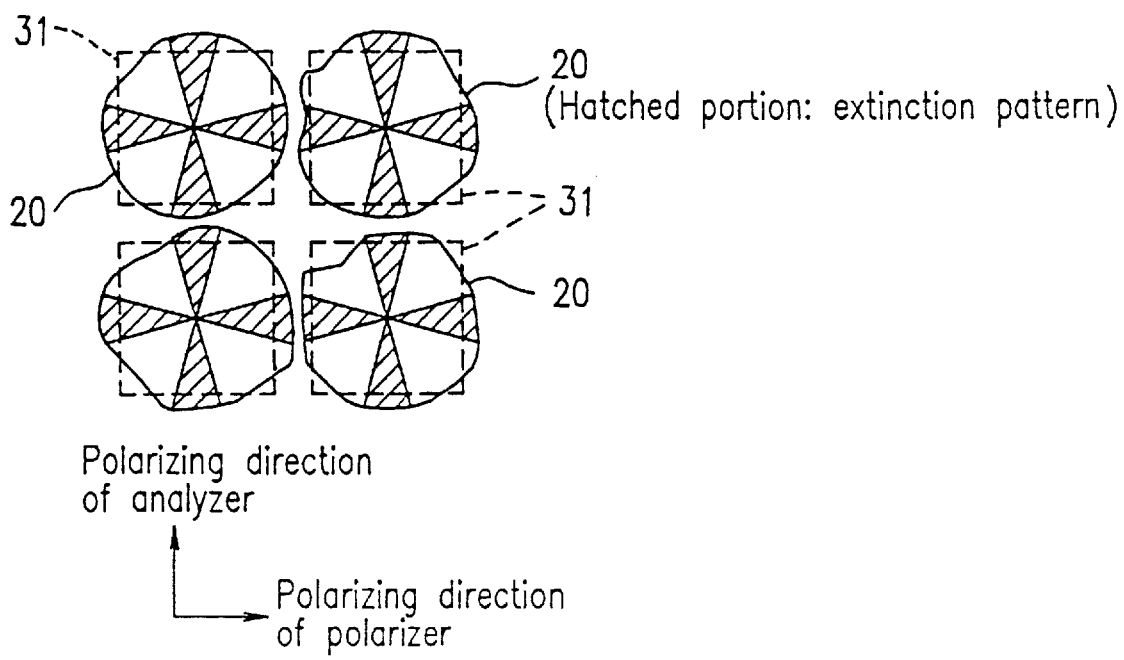
FIG. 8 is a schematic view showing a liquid crystal display device according to an example of the present invention as observed with a polarization micro-scope.

The cell thus produced was observed with a polarization microscope. The observation revealed that, as shown in FIG. 8, liquid crystal regions 20 were formed which substantially reflected the arrangement of the shading portions 31 of the photomask, and that an orientation was obtained which was axially-symmetrical with respect to a center of each liquid crystal region 20.

Next, a polarizing plate was attached on each side of the liquid crystal cell thus produced in such a manner that the polarizing plates were in a crossed-Nicol state. Thus, a liquid crystal device was produced.

The electrooptical characteristics of the liquid crystal display devices were evaluated by measuring the voltage-transmittance characteristics and the response time of the liquid crystal cell by using a liquid crystal characteristics evaluation system LCD-5000 (manufactured by Ohtsuka Electronics, Inc.), against a reference cell obtained by disposing a polarizing plate on each side of the above-mentioned two glass substrates attached to each other in a parallel-Nicol state (in which no liquid crystal material was injected). Herein, the response time is defined as a sum τr+τd (ms) of a rise response time τr (ms) and a fall response time τd (ms). The rise response time τr is defined as a time amount required for the light transmittance to vary by 90% from an initial transmittance when a voltage of 10 V was applied. The fall response time τd is defined as a time amount required for the light transmittance to vary by 90% from a transmittance corresponding to a state of displaying a black image after the application of a voltage was stopped. The steepness of the driving characteristics were evaluated in terms of an absolute value a of a ratio between voltages $V_{90}$ and $V_{10}$ (i.e., $V_{90}/V_{10}$), where $V_{90}$ and $V_{10}$ are defined as voltages that cause a 90% change and a 10% change, respectively, in the light transmittance with respect to the entire range of change of light transmittance.

Figure 9:
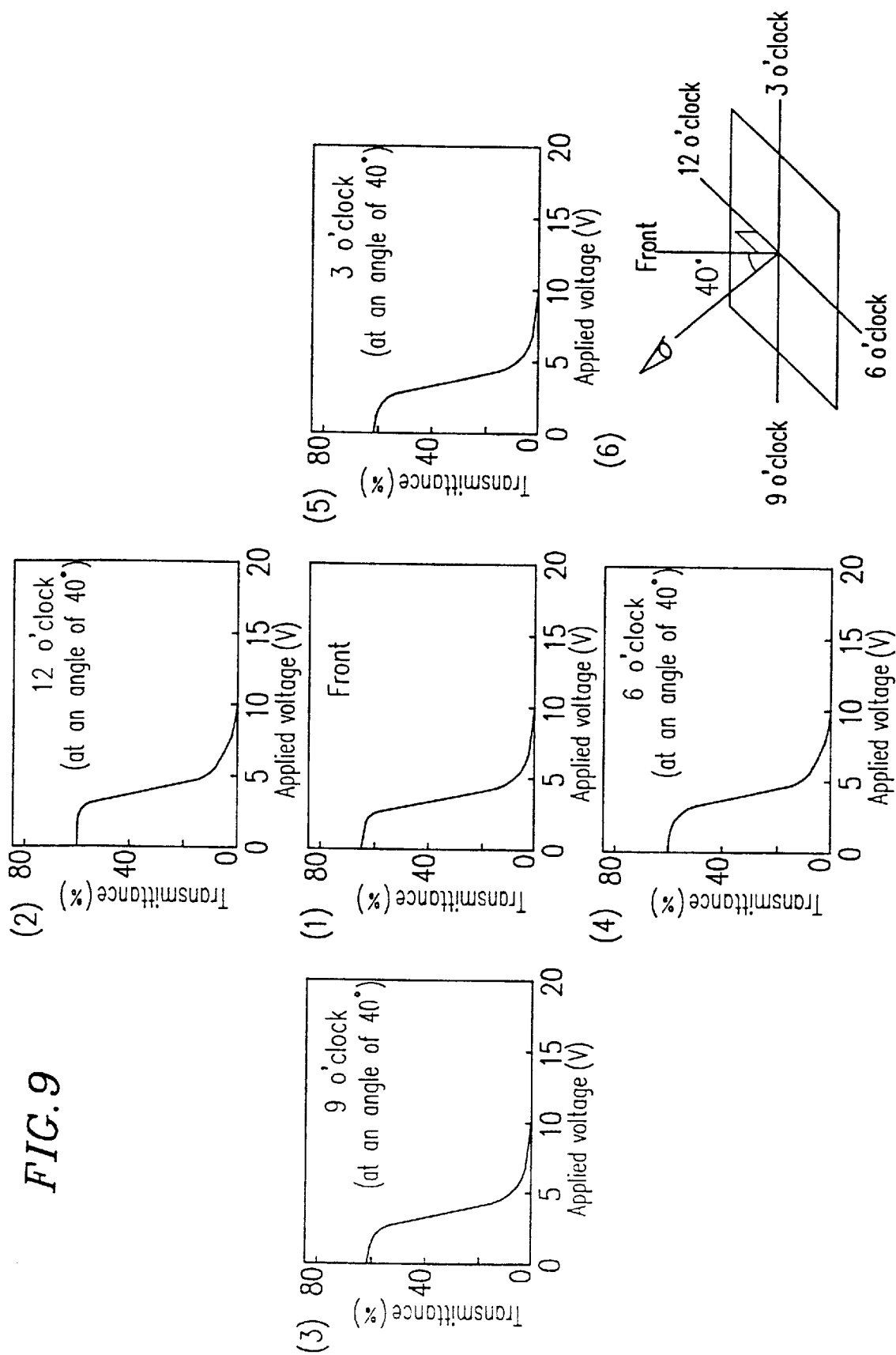
FIG. 9 is a series of graphs showing the electrooptical characteristics (viewing angle characteristics) of a liquid crystal display device according to an example of the present invention.

The measurement results of the electrooptical characteristics of the liquid crystal display devices of Examples 7 and 8, Examples 11 to 14, and Comparative Examples 1 to 4 are shown in Table 7. The voltage-transmittance characteristics of the liquid crystal display device of Example 8 are shown in FIG. 9. The liquid crystal display devices of other Examples had similar tendencies.

TABLE 6

Polymerizable compound used in Examples 7–10

| Compound X | −Y | Example No. |
|---|---|---|
| $CH_2=CHCOO(CH_2)_8O$—⟨◯⟩—⟨◯⟩—Y | $-OCH_2CF_2CF_3$ | 7 |
|  | $-O\ (CH_2)_2(CF_2)_3CF_3$ | 5 |
|  | $-O\ (CH_2)_2(CF_2)_3CF_3$ | 9 |
|  | $-(CF_2)_3CF_3\ <C_4F_9>$ | 10 |

TABLE 7

Electrooptical characteristics of liquid crystal display device

|  | Example 7 | Example 8 | Example 11 | Example 12 | Example 13 | Example 14 | Comparative example 1 | Comparative example 2 | Comparative example 3 | Comparative example 4 |
|---|---|---|---|---|---|---|---|---|---|---|
| Transmittance when no voltage is applied (%) | 65 | 61 | 62 | 63 | 61 | 58 | 94 | 30 | 62 | 60 |
| Transmittance when 10V is applied (%) | 0.6 | 0.7 | 0.6 | 0.5 | 0.4 | 0.6 | 0.1 or less | 1.5 | 0.7 | 0.6 |
| Inversion phenomenon of intermediate gray scale tone | ◯ | ◯ | ◯ | ◯ | ◯ | ◯ | X | Δ | ◯ | ◯ |
| Saturation voltage $V_{90}$ (V) | 5.8 | 5.7 | 5.4 | 5.3 | 5.1 | 5.6 | 4.8 | 8.1 | 7.0 | 6.8 |
| Response time (10 V; ms) | 60 | 58 | 55 | 52 | 47 | 54 | 35 | 330 | 260 | 230 |
| Steepness α | 1.7 | 1.7 | 1.6 | 1.6 | 1.5 | 1.7 | 1.2 | 3.7 | 2.1 | 2.0 |

◯: Substantially no inversion phenomenon observed
Δ: Barely observable inversion phenomenon
X: Easily observable inversion phenomenon Disclination lines were completely prevented from occurring in the liquid crystal display devices of Examples 8 to 10. Only a few disclination lines occurred in the display device of Example 7.

Examples 11 to 14

Liquid crystal display devices (Examples 11–14) were produced using the above-described present polymerizable compound by insulator pattern exposition. Hereinafter, the method of production thereof will be described.

Figure 10A:
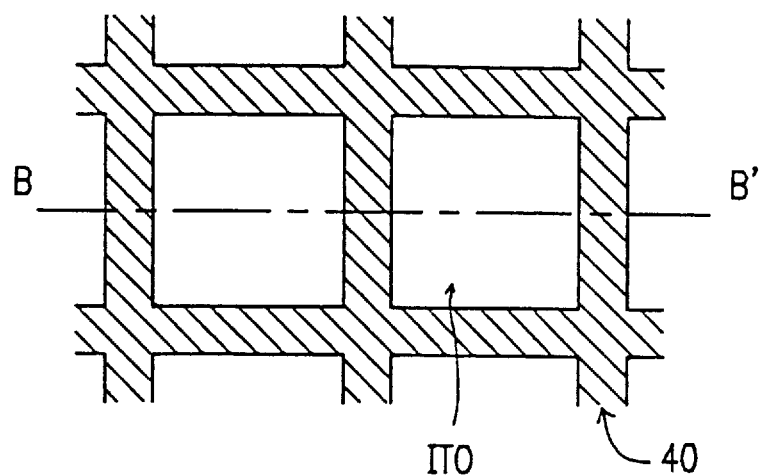
FIG. 10A is a schematic plan view showing a patterned substrate employed in an example of the present invention.
Figure 10B:
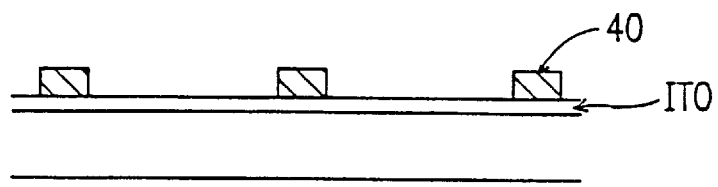
FIG. 10B is a schematic cross-sectional view showing the substrate in FIG. 10A taken at line B–B'.

First and second glass substrates (thickness: 1.1 mm) each having a transparent electrode of ITO (thickness: 50 nm) formed thereon were prepared. The first substrate was subjected to predetermined steps including resist application, baking exposition to light using the photomask 3 shown in FIG. 7, development, rinsing, and further baking. Thereafter, a resist material (OMR83: manufactured by Tokyo Ohka Kogyo co., Ltd.) was applied so as to form a patterned wall 40 of an insulation material as shown in FIGS. 10A (plan view) and 10B (cross-sectional view). The patterned wall 40 was formed in such a manner that regions where the patterned wall 40 was not formed corresponded to pixels. On the second substrate, polyimide (AL4552: manufactured by Japan Synthetic Rubber, Co., Ltd.) was applied as to form an insulation film thereon (unrubbed). A cell was constructed by using the first and second substrates and spacers (average particle diameter: 5 μm) for securing a cell thickness.

The surface free energy levels of the ITO and resist films are 93 mN/m and 35 mN/m, respectively. By utilizing the difference in surface free energy, liquid crystal regions are formed in desired regions corresponding to pixels.

Next, a mixture was prepared by homogeneously mixing the following substances: a photopolymerizable resin composition containing 0.65 g of isobornyl acrylate, 0.15 g of neopentyl diacrylate, and 0.10 g of p-methylstyrene and 0.10 g of polymerizable compound Z shown in Table 8 below; a liquid crystal material containing 13.3 g of ZLI-4792 (manufactured by MERCK KGaA; Δn=0.094); and a photopolymerization initiator consisting of 0.04 g of Irgacure 651 (manufactured by CIBA-GEIGY Corporation). The homogenous mixture was injected into the cell in a vacuum to form a liquid crystal cell.

TABLE 8

Polymerizable compound used in Examples 11–14

| Compound X | −Y | Example No. |
|---|---|---|
| $CH_2=CHCOO(CH_2)_8O$—⟨phenyl⟩—⟨phenyl⟩—Y | −O $(CH_2)_2(CF_2)_3CF_3$ | 11 |
|  | −$(CF_2)_3CF_3$ <$C_4F_9$> | 12 |
|  | −$(CF_2)_5CF_3$ <$C_6F_{13}$> | 13 |
|  | −$(CF_2)_7CF_3$ <$C_8F_{17}$> | 14 |

Thereafter, while maintaining the temperature of the substrate at 110° C. and applying an effective voltage of 2.5 V (60 Hz) between the transparent electrodes, the cell was irradiated with UV rays for 5 minutes through the first substrate under a high-pressure mercury lamp where a power of 10 mW/cm² was obtained, so as to cure the resin composition. Thereafter, the cell was gradually cooled to 40° C. over 5 hours (while continually applying the voltage), further cooled to room temperature (25° C.), and was subjected to further irradiation by using the same UV ray irradiation device so as to prompt the curing.

Finally, two polarizing plates (a polarizer and an analyzer) were attached on the opposing faces of the liquid crystal cell thus fabricated so as to be in a crossed-Nicol state, thus forming a liquid crystal display device having a liquid crystal layer including liquid crystal regions surrounded by a polymer region.

Figure 11:
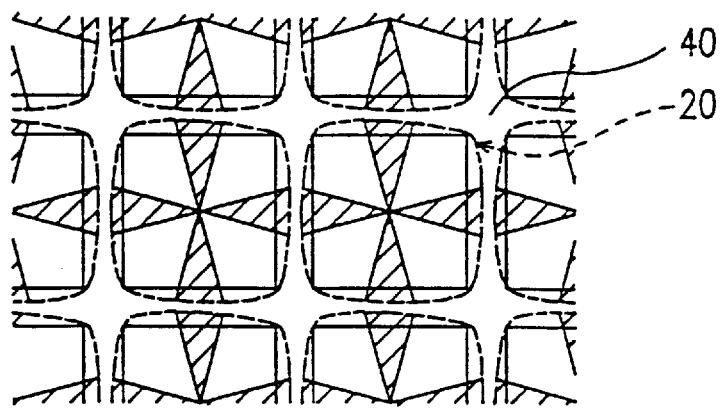
FIG. 11 is a schematic view showing an orientation state of liquid crystal molecules in liquid crystal regions in a liquid crystal display device according to an example of the present invention.

The liquid crystal display devices thus fabricated were observed with a polarizing microscope. The observation showed that, as shown in FIG. 11, a polymer region was formed where the resist pattern 40 existed (i.e., in regions outside the pixels) and that one liquid crystal region 20 was formed in each region corresponding to the ITO, the liquid crystal molecules being oriented in an axis-symmetrical manner in a mono-domain state in each partition. The proof for this was that, when the liquid crystal display device with the above-mentioned two polarizing plates was rotated, only the polymer walls surrounding the liquid crystal regions were observed to be rotating while the position of the schlieren pattern (light extinction pattern) of the liquid crystal regions seemed stationary.

The results of electrooptical characteristics evaluation of the above liquid crystal display devices were as shown in Table 7. These liquid crystal display devices did not exhibit any inversion of images, which is typical of a conventional TN liquid crystal display device (Comparative Example 1; to be described later), or any increase in transmittance at the higher viewing angles when a saturation voltage was applied. Moreover, no roughness was observed in intermediate gray scale tones.

Example 15

A TN-mode liquid crystal display device (Example 15) was produced using the above-described present polymerizable compound. Hereinafter, the method of production thereof will be described.

Glass substrates (thickness: 1.1 mm) each having a transparent electrode of ITO (thickness: 50 nm) formed thereon were prepared. After polyimide (AL4552: manufactured by Japan Synthetic Rubber, Co., Ltd.) was applied on the substrates by spin-coating so as to form alignment films thereon, the substrates were subjected to a predetermined rubbing treatment with nylon cloth. A cell was constructed by attaching these substrates together with LCD spacers (average particle diameter: 5 $\mu$m) for securing a cell thickness in such a manner that the rubbing directions thereof were perpendicular to each other.

The photomask 3 shown in FIG. 7 was disposed on the cell thus fabricated. Furthermore, a mixture containing the polymerizable resin composition used in Example 8, a liquid crystal material ZLI-4792 (manufactured by MERCK KGaA; $\Delta$n=0.094), and a photopolymerization initiator Irgacure 651 at the same ratio as in Example 8 was injected into the cell by capillary action. Then, a liquid crystal cell having a liquid crystal layer including liquid crystal regions surrounded by a polymer region was fabricated by the same method as in the above Examples of the present invention.

A TN-mode liquid crystal display device was obtained with two polarizers attached in such a manner that the polarizing axes thereof coincided with the rubbing directions.

The liquid crystal material in the liquid crystal display device fabricated in the present Example showed a uniform TN orientation. Since the liquid crystal regions in the liquid crystal display device of the present Example are surrounded by the polymer region, the display characteristics of the display device did not change even when the display surface was pressed with a pen or the like, indicative of a remarkably improved pressure resistance as compared with a conventional TN-mode liquid crystal display device of Comparative Example 1 (described later).

Example 16

An STN-mode liquid crystal display device (Example 16) was produced using the above-described present polymerizable compound. Hereinafter, the method of production thereof will be described.

Glass substrates (thickness: 1.1 mm) each having a transparent electrode of ITO (thickness: 50 nm) formed thereon were prepared. After polyimide (Sunever: manufactured by Nissan Chemical Industries, Ltd.) as applied on the substrates by spin-coating so as to form alignment films thereon, the substrates were subjected to a predetermined rubbing treatment with nylon cloth. A cell was constructed by attaching these substrates together with LCD spacers (average particle diameter: 9 $\mu$m) for securing a cell thickness in such a manner that the rubbing directions thereof constituted 240°.

The photomask 3 shown in FIG. 7 was disposed on the cell thus fabricated. Furthermore, a mixture containing the polymerizable resin composition used in Example 7, a liquid crystal material ZLI-4427 (manufactured by MERCK KGaA) and a photopolymerization initiator Irgacure 651 at the same ratio as in Example 7 was injected into the cell by capillary action. Then, a liquid crystal cell having a liquid crystal layer including liquid crystal regions surrounded by a polymer region was fabricated by the same method as in the above Examples of the present invention.

An STN-mode liquid crystal display device was obtained with two polarizers attached in such a manner that the polarizing axes thereof constituted 105° with each other and constituted 45° with their corresponding rubbing directions.

The liquid crystal material in the liquid crystal display device fabricated in the present Example showed a uniform STN orientation. Since the liquid crystal regions in the liquid crystal display device of the present Example are surrounded by the polymer region, the display characteristics of the display device did not change even when the display surface was pressed with a pen or the like, indicative of a remarkably improved pressure resistance as compared with a conventional STN liquid crystal display device.

Example 17

An FLC-mode (SSF type orientation) liquid crystal display device (Example 17) was produced using the above-described present polymerizable compound. Hereinafter, the method of production thereof will be described.

Glass substrates (thickness: 1.1 mm) each having a transparent electrode of ITO (thickness: 50 nm) formed thereon were prepared. After polyimide (Sunever: manufactured by Nissan Chemical Industries, Ltd.) was applied on the substrates by spin-coating so as to form alignment films thereon, the substrates were subjected to a predetermined rubbing treatment with nylon cloth. A cell was constructed by attaching these substrates together with LCD spacers (average particle diameter: 2 $\mu$m) for securing a cell thickness in such a manner that the rubbing directions thereof were perpendicular with each other.

The photomask 3 shown in FIG. 7 was disposed on the cell thus fabricated. Furthermore, a mixture was prepared by homogeneously mixing the following substances: a polymerizable resin composition containing 0.02 g of polyethyleneglycoldiacrylate (NK ESTER A-200: manufactured by Shin-Nakamura Chemical Co., Ltd.), 0.09 g of laurylacrylate, 0.01 g of styrene and 0.80 g of compound X used in Example 10; a liquid crystal material containing 0.80 g of ZLI-4003 (manufactured by MERCK KGaA); and a photopolymerization initiator consisting of 0.005 g of Irgacure 651. The homogenous mixture was injected, while heated, into the cell in a vacuum under a reduced pressure. Then, a liquid crystal cell having a liquid crystal layer including liquid crystal regions surrounded by a polymer region was fabricated by the same method as in the above Examples of the present invention.

An FLC-mode (SSF type orientation) liquid crystal display device was obtained with two polarizers attached in such a manner that the polarizing axes thereof constituted 90° with each other.

The liquid crystal material in the liquid crystal display device fabricated in the present Example showed a uniform SSF orientation when observed with a polarization microscope. Since the liquid crystal regions in the liquid crystal display device of the present Example are surrounded by the polymer region, the display characteristics of the display device did not change even when the display surface was pressed with a pen or the like. Moreover, any disadvantageous disorientation due to extrinsic force, which is observed in conventional FLC-mode liquid crystal display devices, was not observed in the liquid crystal display device of the present Example, indicating that a rapid-response liquid crystal display device with remarkably improved pressure resistance was obtained.

Comparative Examples

Hereinafter, Comparative Examples that are useful for clarifying the effects of the above embodiments of the present invention will be described.

Comparative Example 1

A conventional TN-mode liquid crystal display device was produced.

Glass substrates similar to those of Example 7, each having a transparent electrode of ITO formed thereon, were prepared. After polyimide AL4552 (manufactured by Japan Synthetic Rubber, Co., Ltd.) was applied on the substrates so as to form insulation films thereon, the substrates were subjected to a predetermined rubbing treatment with nylon cloth. A cell was constructed by attaching these substrates together with LCD spacers (average particle diameter: 5 μm) for securing a cell thickness in such a manner that the rubbing directions thereof were perpendicular to each other, as in Example 7.

A liquid crystal material similar to Example 7 containing ZLI-4792 (with 0.3% by weight of a chiral agent S811 added thereto; manufactured by MERCK KGaA) was injected into the cell thus fabricated to form a liquid crystal cell.

Next, two polarizers were attached so as to interpose the liquid crystal cell in such a manner that the polarizing axes thereof coincided with the rubbing directions and that they were in a crossed-Nicol state, whereby a conventional TN-mode liquid crystal display device was obtained.

Figure 12:
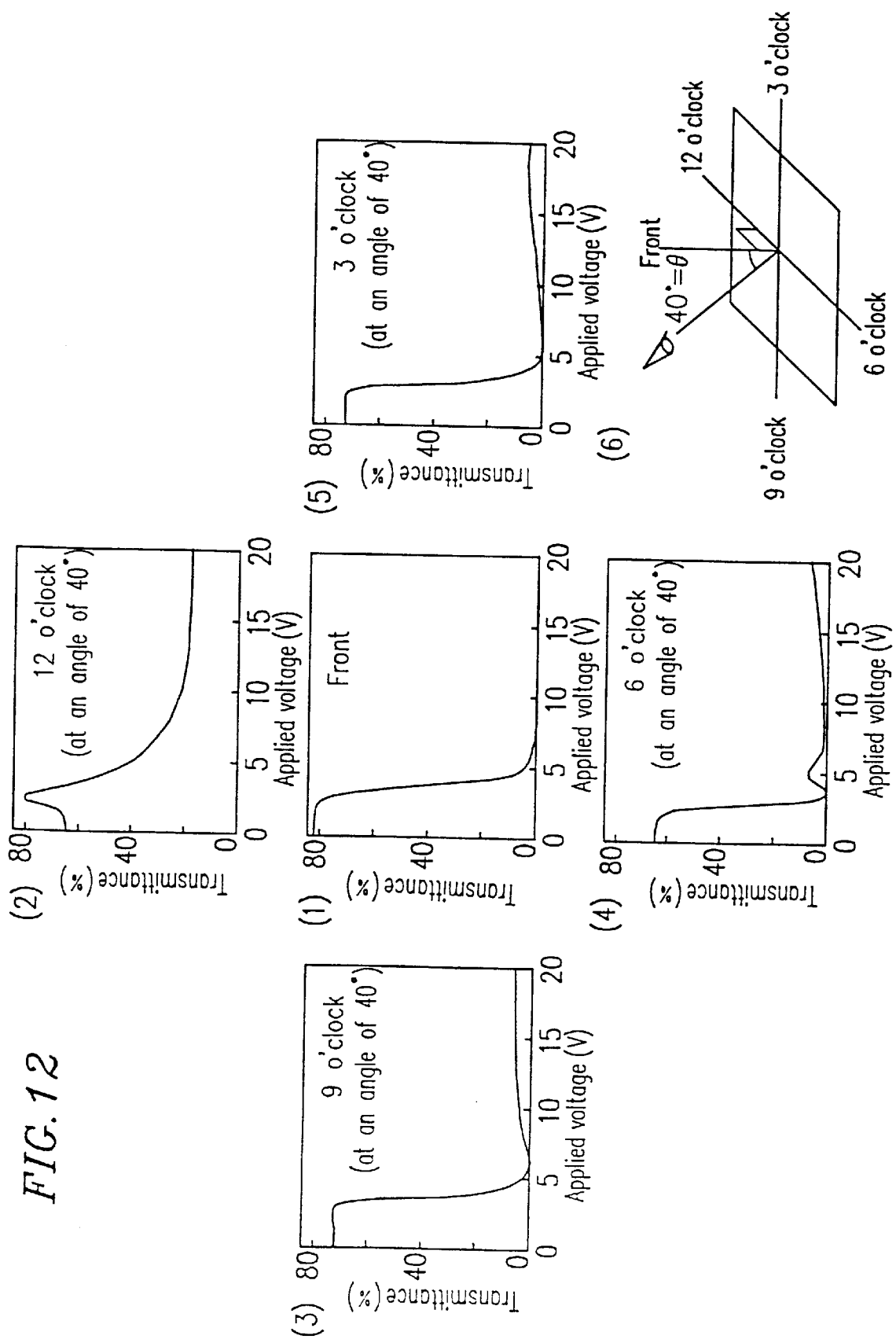
FIG. 12 is a series of graphs showing the electrooptical characteristics (viewing angle characteristics) of a conventional TN-mode liquid crystal display device.
Figure 13A:
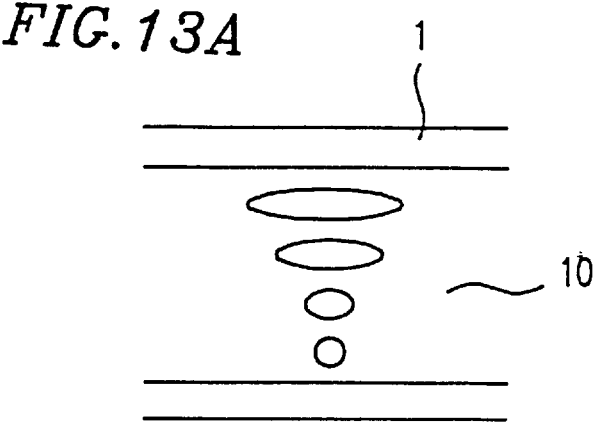
FIGS. 13A to 13C are schematic views showing the change in contrast depending on the viewing angle of a TN-mode liquid crystal display device.
Figure 13B:
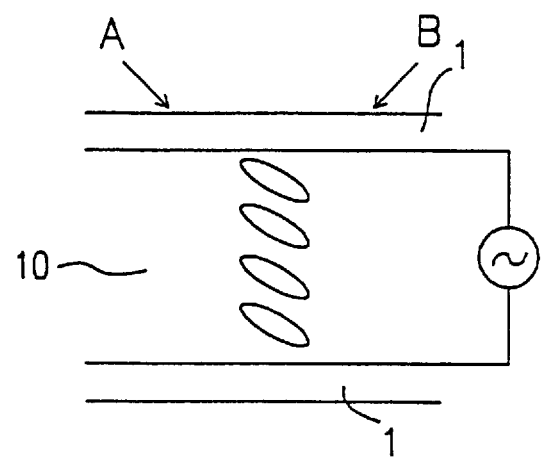
Figure 13C:
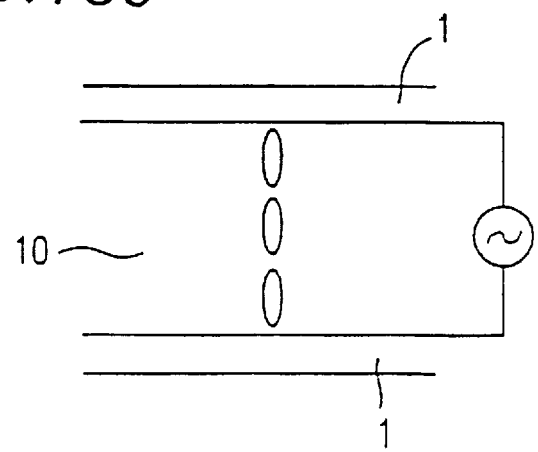
Figure 14A:
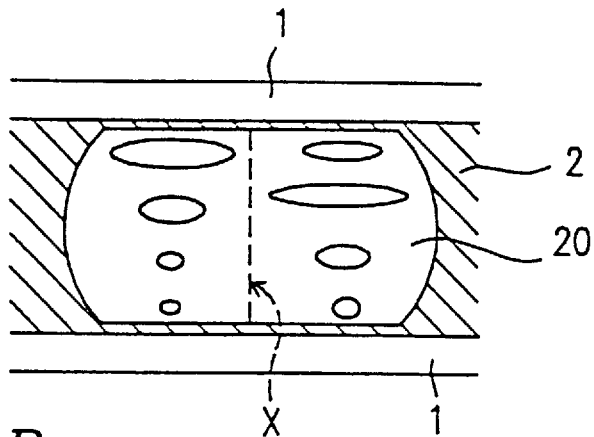
FIGS. 14A to 14C are schematic views showing the change in contrast depending on the viewing angle of a liquid crystal display device of a wide viewing angle mode.
Figure 14B:
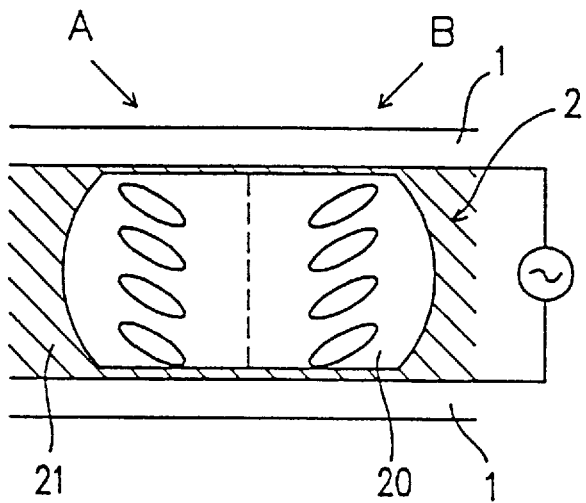
Figure 14C:
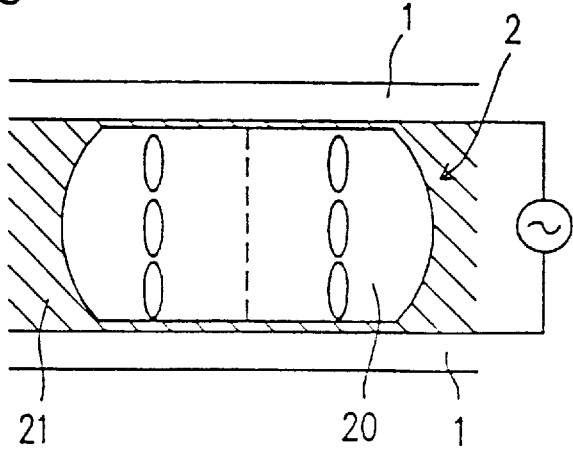

The electrooptical characteristics of the above display device are shown in Table 7, and the viewing angle characteristics thereof are shown in FIG. 12. As seen from FIG. 12, an inversion of image occurs when the conventional TN-mode liquid crystal display device displays an intermediate gray scale tone.

Comparative Example 2

A liquid crystal display device was produced using a polymerizable resin composition which did not contain the present polymerizable compound.

The photomask 3 shown in FIG. 7 was placed on an empty cell fabricated as described in Example 7. A mixture was prepared by homogeneously mixing the following substances: a polymerizable resin composition containing 0.75 g of stearylacrylate, 0.15 g of 1,4-butanediol, and 0.10 g of p-phenylstyrene; a liquid crystal material containing 13.3 g of ZLI-4792 (manufactured by MERCK KGaA; Δn=0.094); and a photopolymerization initiator consisting of 0.04 g of Irgacure 651. The homogenous mixture was injected into the cell by capillary action. Then, a liquid crystal cell was manufactured by allowing a photopolymerization phase separation to progress by exposition to UV rays through a photomask while applying a voltage thereto as in Examples 7 to 10 to form a liquid crystal cell. Next, polarizers were attached to the liquid crystal cell in a crossed-Nicol state to form a liquid crystal display device.

The electrooptical characteristics of the liquid crystal display device thus produced were evaluated in the same manner as in Example 7. The evaluation results are shown in Table 7.

In the liquid crystal cell of Comparative Example 2, the phase separation between the liquid crystal and the polymer was insufficient and some resin material is observed to be present in the liquid crystal regions. Moreover, disclination lines were observed when a voltage was applied, thereby resulting in unsatisfactory display characteristics. The display device had a transmittance of 1.5% when a voltage of 10 V was applied, which value is larger than that of the liquid crystal cells of Examples 7 to 14. This is in large part ascribed to the generation of disclination lines.

Comparative Examples 3 and 4

Liquid crystal display devices (Comparative Examples 3 and 4) were produced by using a polymerizable resin composition containing a polymerizable compound having a structure similar to that of liquid crystal in its molecule.

As in Example 11, an insulation material was patterned on a first glass substrate. A cell was constructed by attaching the first and second substrates together with LCD spacers (average particle diameter: 5 μm) for securing a cell thickness. A mixture was prepared by homogeneously mixing the following substances: a photopolymerizable resin material containing 0.65 g of isobornyl acrylate, 0.15 g of neopentyl diacrylate, and 0.10 g of p-methylstyrene and 0.10 g of polymerizable compound A shown in Table 9 below; a liquid crystal material containing 13.3 g of ZLI-4792 (manufactured by MERCK KGaA; Δn=0.094); and a photopolymerization initiator consisting of 0.04 g of Irgacure 651. The homogenous mixture was injected into the cell under a reduced pressure.

TABLE 9

Polymerizable compound used in Comparative examples 3 and 4

| Compound X | −Y | Comparative example No. |
|---|---|---|
| $CH_2=CHCOO(CH_2)_8O$ 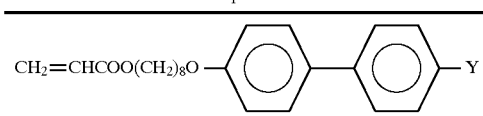 | 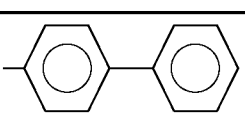 | 3 |

TABLE 9-continued

Polymerizable compound used in Comparative examples 3 and 4

| Compound X | −Y | Comparative example No. |
|---|---|---|
| 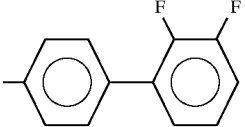 | | 4 |

Then, a liquid crystal cell was manufactured by allowing a photopolymerization phase separation to progress by exposition to UV rays through a photomask while applying a voltage thereto as in Examples 11 to 14 to form a liquid crystal cell. Next, polarizers were attached to the liquid crystal cell in a crossed-Nicol state to form a liquid crystal display device.

The electrooptical characteristics of the liquid crystal display devices thus produced were evaluated in the same manner as in Example 11 and the like. The evaluation results are shown in Table 7.

An observation of the liquid crystal cells of Comparative Examples 3 and 4 with a polarization micro-scope revealed that disclination lines were prevented from occurring when a voltage was applied due to the addition of the polymerizable compound having a structure similar to that of liquid crystal in its molecule. As a result, the transmittance when a voltage of 10 V was applied was 0.7%, indicative of a relatively good black display. However, as compared with the liquid crystal display devices of the above Examples 7 to 17, the liquid crystal display devices of Comparative Examples 3 and 4 had an unsatisfactory response time τr+τd and an insufficient α value representing the driving characteristics steepness. Thus, it will be appreciated that the present polymerizable compound can effectively solve the problems stated herein.

Comparative Examples make it clear that a liquid crystal display device using the present polymerizable compound can have improved display characteristics when display a black image, as well as improved response time and improved threshold characteristics and steepness of the voltage-transmittance characteristics.

As described above, by employing the present polymerizable compound having a structure similar to that of liquid crystal within its molecule and having a fluorinated alkyl group introduced at one end of its molecule, it becomes possible to improve the separation between the liquid crystal and the polymerizable compound in a liquid crystal display device composed of a liquid crystal-polymer complex and liquid crystal regions having an axially symmetrical orientation, thereby preventing the polymerizable compound from being mixed into the liquid crystal material and reducing the anchoring of liquid crystal molecules to the polymer region.

In a liquid crystal display device produced by using the present polymerizable compound, disclination lines can be prevented from occurring when a voltage is applied, thereby remarkably improving the black display level and therefore the contrast of the liquid crystal display device. Moreover, in accordance with the present liquid crystal display device, the orientation of liquid crystal molecules is stabilized, thereby resulting in a uniform orientation. In addition, the problems of unsatisfactory response time and insufficient threshold characteristics and steepness of the voltage-transmittance characteristics associated with the use of a conventional polymerizable compound are substantially solved.

Furthermore, in the liquid crystal display device of the present invention, liquid crystal molecules have an axially symmetrical orientation, resulting in good viewing angle characteristics, and a polymer region (typically a polymer wall) is included in the cell, resulting in good pressure resistance. In particular, the liquid crystal display device of the present invention can be applied to a broad range of devices such as large-area display devices and pen-input type liquid crystal display devices. Furthermore, the polymer region of the liquid crystal display device of the present invention is formed from a monomer containing a polymerizable compound capable of improving the orientation restriction force of the substrate. This results in an excellent axially-symmetrical orientation state of liquid crystal molecules in the liquid crystal regions of a liquid crystal display device in which the liquid crystal molecules are oriented by utilizing the orientation restriction force of the substrate, and the display device shows a remarkably improved pressure resistance against an extrinsic pressure, e.g., the pressure occurring with an input operation using a pen-type device. Thus, a flat display having excellent viewing characteristics and display quality can be provided.

The liquid crystal display device of the present invention can be typically used for displays of personal computers, word processors, liquid crystal television sets, and display panels for automobile navigation systems, particularly taking advantage of its broad viewing angle characteristics.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A polymerizable compound represented by Formula (I):

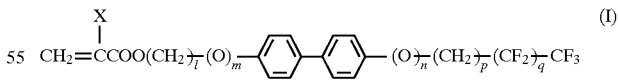

where x represents a hydrogen atom or a methyl group; 1 represents an integer in the range of 0 to 14; m represents 0 or 1; n represents 0 or 1; p represents 0 [an integer in the range of 0 to 6]; and q represents an integer in the range of 3 to 7, wherein m is 0 under the condition 1=0, and 1 under the condition 1≠0.

2. A polymerizable compound according to claim 1, wherein 1≠0 in Formula (I).

3. A liquid crystal display device including a pair of substrates, at least one of the substrates being transparent, and a liquid crystal layer having a liquid crystal region surrounded by a polymer region, the liquid crystal layer being interposed between the pair of substrates, wherein the polymer region is formed from a monomer at least comprising the polymerizable compound according to claim 2.

4. A liquid crystal display device including a pair of substrates, at least one of the substrates being transparent, and a liquid crystal layer having a liquid crystal region surrounded by a polymer region, the liquid crystal layer being interposed between the pair of substrates, wherein the polymer region is formed from a monomer at least comprising the polymerizable compound represented by formula (I):

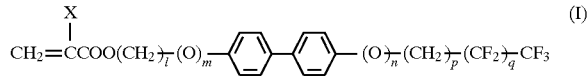

where x represents a hydrogen atom or a methyl group; 1 represents an integer in the range of 0 to 14: m represents 0 or 1 n represents 0 or 1: p represents an integer in the range of 0 to 6; and q represents an integer in the range of 0 to 9, wherein m is 0 under the condition l=0, and 1 under the condition l≠0.

5. A liquid crystal display device according to claim 4, wherein liquid crystal molecules in the liquid crystal region have an axially-symmetrical, radial, concentric, random, or spiral orientation.

6. A liquid crystal display device according to claim 5, wherein the polymer region has a function of restricting an orientation state of the liquid crystal molecules with respect at least one of the pair of substrates.

7. A liquid crystal display device according to claim 4, wherein the polymer region has a function of restricting an orientation state of the liquid crystal molecules with respect at least one of the pair of substrates.

8. A liquid crystal display device according to claim 4, further including an insulation film/alignment layer for achieving a uniaxial and uniform orientation state of the liquid crystal molecules corresponding to the liquid crystal region, the insulation film/alignment layer being provided on at least one of the pair of substrates, wherein the orientation state of the liquid crystal region and the entire liquid crystal display device are adapted for a TN, STN, ECB, or an SSFLC mode.

9. A liquid crystal composition for display comprising a polymerizable monomer according to claim 1 and a liquid crystal material.

* * * * *

UNITED STATES PATENT AND TRADEMARK OFFICE
CERTIFICATE OF CORRECTION

PATENT NO. : 5,814,378
DATED : September 29, 1998
INVENTOR(S) : Onishi, et al

It is certified that error appears in the above-identified patent and that said Letters Patent is hereby corrected as shown below:

In Column 18, line 55, please replace:

with:

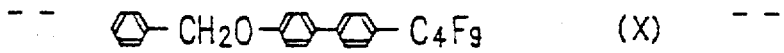

In Column 19, line 25, please replace:

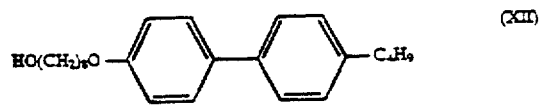

UNITED STATES PATENT AND TRADEMARK OFFICE
CERTIFICATE OF CORRECTION

PATENT NO. : 5,814,378  
DATED : September 29, 1998  
INVENTOR(S) : Onishi, et al It is certified that error appears in the above-identified patent and that said Letters Patent is hereby corrected as shown below:

with:

In Column 20, line 6, please replace:

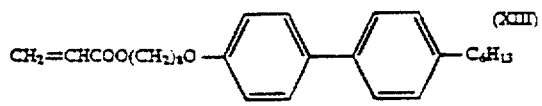

UNITED STATES PATENT AND TRADEMARK OFFICE
CERTIFICATE OF CORRECTION

PATENT NO. : 5,814,378
DATED : September 29, 1998
INVENTOR(S) : Onishi, et al

It is certified that error appears in the above-identified patent and that said Letters Patent is hereby corrected as shown below:

with:

(XIII) --

In Column 23, please replace:

TABLE 6

Polymerizable compound used in Examples 7-10

| Compound X | −Y | Example No. |
|---|---|---|
| 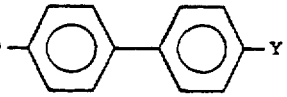 | −OCH$_2$CF$_2$CF$_3$ | 7 |
| | −O(CH$_2$)$_2$(CF$_2$)$_3$CF$_3$ | 8 |
| | −O(CH$_2$)$_2$(CF$_2$)$_3$CF$_3$ | 9 |
| | −(CF$_2$)$_3$CF$_3$ <C$_4$F$_9$> | 10 |

UNITED STATES PATENT AND TRADEMARK OFFICE
CERTIFICATE OF CORRECTION

PATENT NO. : 5,814,378
DATED : September 29, 1998
INVENTOR(S) : Onishi, et al

It is certified that error appears in the above-identified patent and that said Letters Patent is hereby corrected as shown below:

with:

TABLE 6

Polymerizable compound used in Examples 7-10

| Compound X | -Y | Example No. |
|---|---|---|
| $CH_2=CHCOO(CH_2)_8O-\bigcirc-\bigcirc-Y$ | $-OCH_2CF_2CF_3$ | 7 |
| | $-O(CH_2)_2(CF_2)_3CF_3$ | 8 |
| | $-O(CH_2)_2(CF_2)_3CF_3$ | 9 |
| | $-(CF_2)_3CF_3 \;\; <C_4F_9>$ | 10 |

In Column 30, please replace:

TABLE 9

Polymerizable compound used in Comparative examples 3 and 4

| Compound X | -Y | Comparative example No. |
|---|---|---|
| $CH_2=CHCOO(CH_2)_8O-\bigcirc-\bigcirc-Y$ | $-\bigcirc-\bigcirc$ | 3 |

UNITED STATES PATENT AND TRADEMARK OFFICE
CERTIFICATE OF CORRECTION

PATENT NO. : 5,814,378
DATED : September 29, 1998
INVENTOR(S) : Onishi, et al

It is certified that error appears in the above-identified patent and that said Letters Patent is hereby corrected as shown below:

with:

-- TABLE 9

Polymerizable compound used in Comparative examples 3 and 4

| Compound X | −Y | Comparative example No. |
|---|---|---|
| $CH_2=CHCOO(CH_2)_8O-Y$ | ⟨O⟩-⟨O⟩ | 3 |
| | ⟨O⟩-⟨O⟩ (F, F) | 4 |

--

In Column 33, claim 4, lines 18-19 please replace "in the range of 0 to 14: m represents 0 or 1 n represents 0 or 1:" with --in the range of 0 to 14; m represents 0 or 1; n represent 0 or 1;--

Signed and Sealed this

Twenty-seventh Day of April, 1999

UNITED STATES PATENT AND TRADEMARK OFFICE
CERTIFICATE OF CORRECTION

PATENT NO. : 5,814,378

DATED : September 29, 1998

INVENTOR(S) :
Onishi, et al.

It is certified that error appears in the above-identified patent and that said Letters Patent is hereby corrected as shown below:

Column 32, lines 59-60, delete "[an integer in the range of 0 to 6]".

Signed and Sealed this

Eighth Day of June, 1999

Attest:

Q. TODD DICKINSON

*Attesting Officer*      *Acting Commissioner of Patents and Trademarks*